United States Patent [19]

Saxholm

[11] 4,324,859

[45] * Apr. 13, 1982

[54] APPARATUS AND ASSOCIATED METHODS FOR USE IN MICROBIOLOGICAL, SEROLOGICAL, IMMUNOLOGICAL, CLINICAL-CHEMICAL AND SIMILAR LABORATORY WORK

[76] Inventor: Rolf Saxholm, Box 3, 1362 Billingstad, Norway

[*] Notice: The portion of the term of this patent subsequent to Feb. 12, 1974, has been disclaimed.

[21] Appl. No.: 12,905

[22] Filed: Feb. 16, 1979

Related U.S. Application Data

[60] Continuation-in-part of Ser. No. 731,103, Oct. 8, 1976, Pat. No. 4,140,582, which is a continuation of Ser. No. 602,745, Aug. 7, 1975, Pat. No. 3,985,608, which is a continuation of Ser. No. 414,939, Nov. 12, 1973, abandoned, which is a division of Ser. No. 33,594, May 1, 1970, Pat. No. 3,791,930.

[30] Foreign Application Priority Data

May 3, 1969 [NO] Norway .................................. 691832

[51] Int. Cl.³ ............................................ C12Q 1/20

[52] U.S. Cl. ..................... 435/33; 23/230 B; 422/102; 435/32; 435/34; 435/287; 435/299; 435/300; 435/301; 435/7

[58] Field of Search .................. 435/7, 29, 30, 32, 33, 435/34, 35, 36, 37, 38, 39, 40, 287, 288, 292, 293, 299, 300, 301, 317, 805; 422/102; 23/230 B

[56] References Cited

U.S. PATENT DOCUMENTS

| | | | |
|---|---|---|---|
| 3,415,361 | 12/1968 | Adams, Jr. et al. | 435/301 X |
| 3,791,930 | 2/1974 | Saxholm | 435/291 X |
| 3,985,608 | 10/1976 | Saxholm | 435/32 X |
| 4,140,582 | 2/1979 | Saxholm | 435/291 |

Primary Examiner—Robert J. Warden

[57] ABSTRACT

For microbiological and other laboratory work in which an active substance is contacted with a substrate there is provided a container for the substrate and a divided carrying body with respective separated sections in sealed contact within the container such that the sections form separate regions with isolated substrate portions in each of the regions. The active substance is supported by the carrying body and is immersed in the respective isolated substrate regions so that it can be diffused into the substrate portions.

65 Claims, 39 Drawing Figures

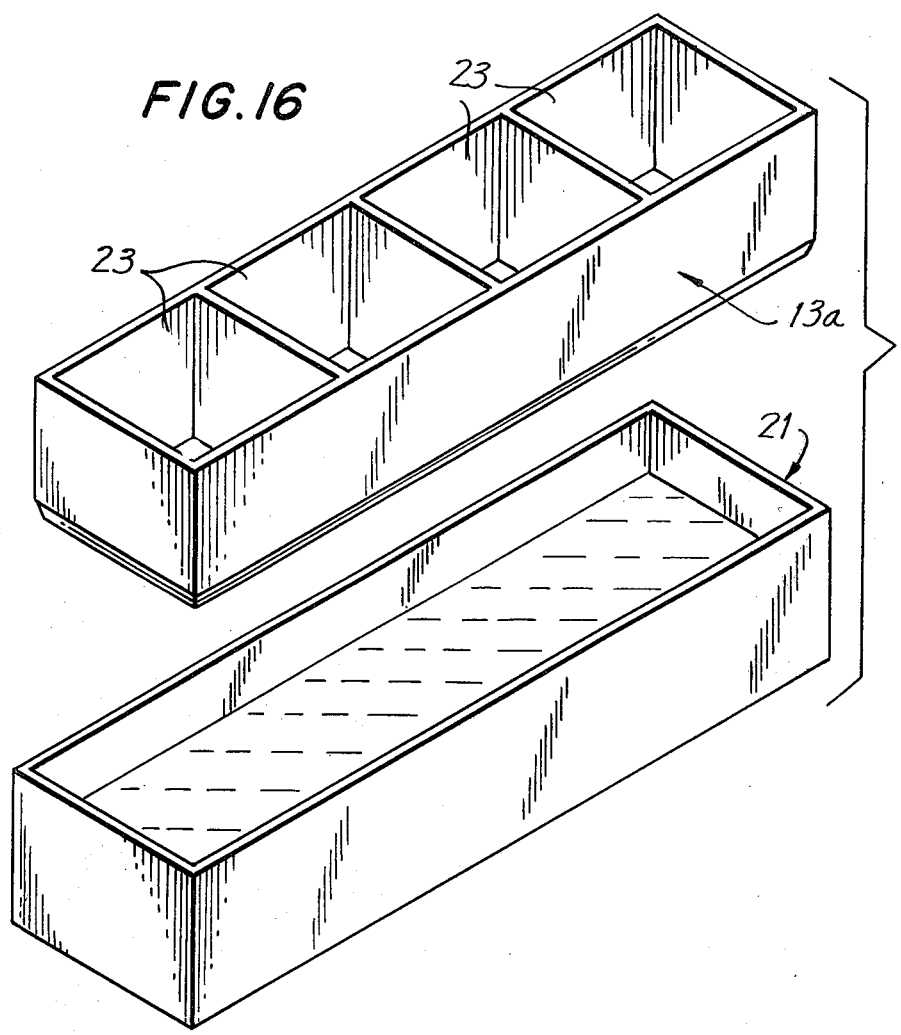
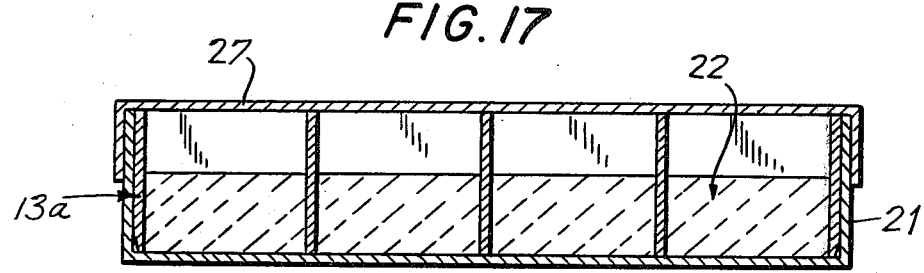

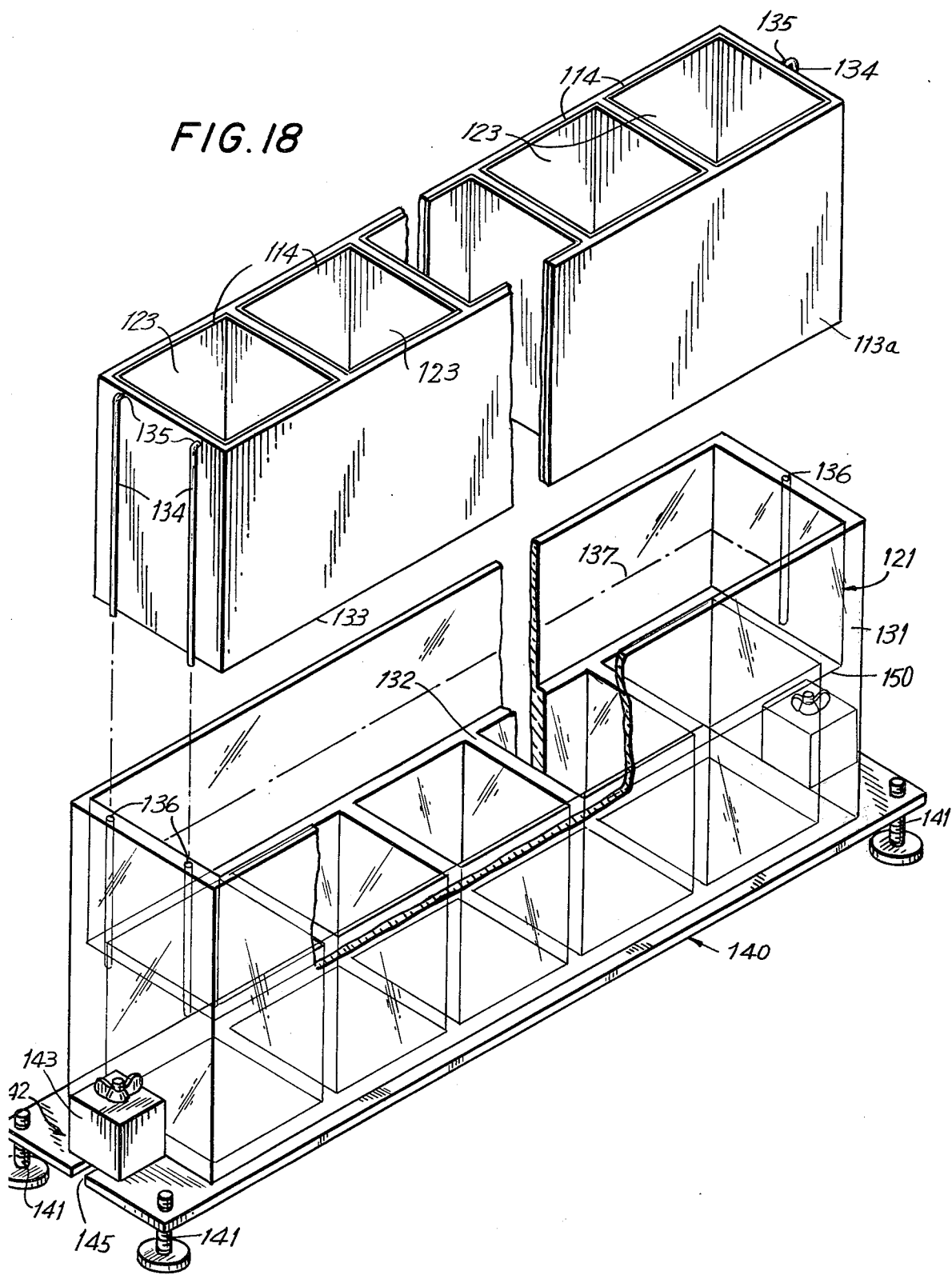

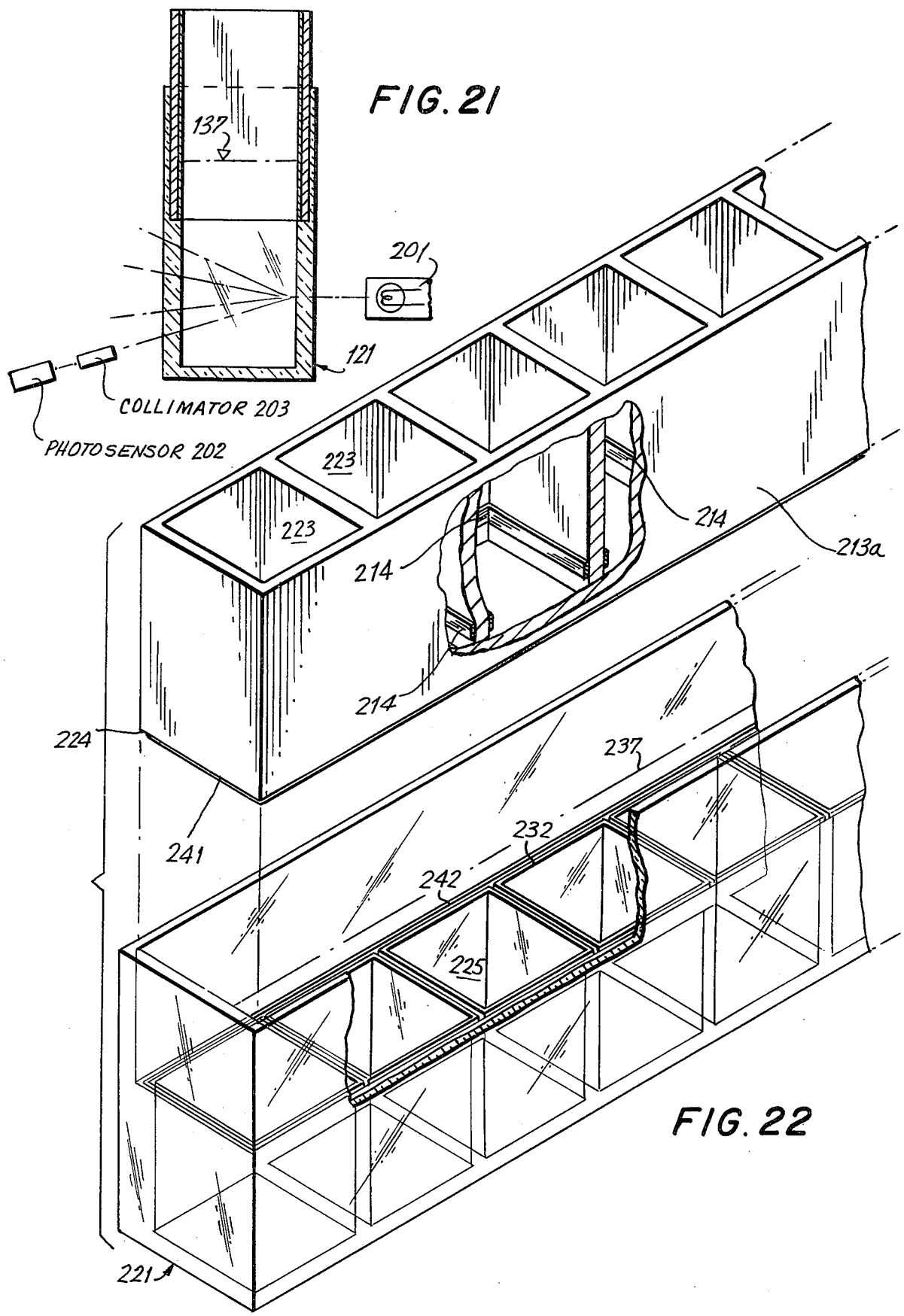

APPARATUS AND ASSOCIATED METHODS FOR USE IN MICROBIOLOGICAL, SEROLOGICAL, IMMUNOLOGICAL, CLINICAL-CHEMICAL AND SIMILAR LABORATORY WORK

CROSS-RELATED APPLICATION

This application is a continuation-in-part of Ser. No. 731,103 filed Oct. 8, 1976 now U.S. Pat. No. 4,140,582 which is in turn a continuation of Ser. No. 602,745 filed Aug. 7, 1975 and issued as U.S. Pat. No. 3,985,608 which is in turn a continuation of Ser. No. 414,939 filed Nov. 12, 1973 now abandoned which in turn is a division of Ser. No. 33,594 filed May 1, 1970 issued as U.S. Pat. No. 3,791,930.

BACKGROUND OF THE INVENTION

This invention relates to a new technique permitting rationalization and automation of microbiological, serological, immunological, clinical-chemical and similar laboratory work.

Before the invention is explained, it will be expedient to give some general background information.

Bacteria are grown in substrates (media) which are either liquid (broth) or of more or less solid consistency. Growth in liquid substrates takes place throughout the entire substrate, while in solid substrates the growth usually takes place on the surface.

The solid substrates are made from the liquid by adding agar (or some other substance, such as gelatine) in various concentrations, or through the coagulation of albumin. There are a number of different types of liquid and solid substrates. Often they have a common basic composition, but otherwise the composition changes according to which substances are required for the growth of the bacteria in question.

Many, though not all, bacteria decompose and utilize matter in different ways. This can be registered by various chemical or physico-chemical reactions. As an example may be mentioned the fermentation or splitting of various types of so-called "sugar" (hereinafter called sugar) by bacteria. This fermentation, considered for the whole series of sugar types in question, is often characteristic of the individual type of bacterium, and frequently differs from one bacterium to the other. This circumstance is widely exploited as an aid in distinguishing bacteria from one another.

When a bacterium decomposes a sugar to acid products, the pH value in the substrate decreases, as may be observed by a change in the color of an added indicator. If, for example, a sugar is added to a solid substrate as a fermentation basis, and bromothymol blue is added as an indicator, the result of inoculation with bacteria that break down sugar, and with bacteria that do not, is as follows; The sugar-splitting bacteria will grow on the surface of the substrate and form yellow colonies, while the non-splitting bacteria will form colonies of the same blue color as that of the substrate before inoculation. Yellow and blue colonies may lie close together, side by side, on the surface of the substrate.

A corresponding liquid substrate will change its color to yellow if sugar-splitting bacteria grow in it, and will remain blue if the growth is purely of non-splitting bacteria.

When, as an aid to classification, fermentation determinations are carried out, liquid substrates are usually employed.

Since one of the objects of the invention is to rationalize fermentation tests-without limiting its scope to this field-a more detailed description will be given of how a fermentation test is carried out according to a known method.

A pure culture of the micro-organism to be classified by the fermentation test must be prepared. Samples from this pure culture are inoculated into broths which have already been poured into test tubes. These broths contain an indicator and various types of sugar. The test tubes are closed with plugs or caps. The test tubes containing the broths are placed in racks and incubated for growth and reaction. The result is read by inspecting each tube, and is noted by hand.

This method requires that the test tubes be placed in the racks by hand. Each tube of broth contains only one kind of sugar, but the number of kinds of sugar, and thus of tubes, may often be comparatively high. This means that handling the tubes and segregating them according to type of sugar when they are to be arranged in rows in the racks, can be a relatively laborious process. Furthermore, there is room for confusion and error.

The inoculation process is also relatively laborious. The inoculation of each test tube containing the sugar broth involves removal of the stopper, the upper edge of the tube being sterilized by a flame to remove any possible microbial contamination, and the stopper being replaced.

The test tubes, which are often of glass, must, after having been read, go through a time-consuming and laborious process before they can be used anew. First they are put in an autoclave to kill the cultures. Then they are emptied, washed, and rinsed, whereupon they are fitted with stoppers. After this they are sterilized and are once again ready to receive new charges of broths containing various types of sugar and indicator.

The preparation of the substrates to be put into the test tubes also demands time and labor. First, the broth must be prepared and then, to portions of this, a number of different types of sugar have to be added. These mixtures are then poured into test tubes and duly sterilized. The tubes are marked to indicate the type of sugar therein. They are then placed in a refrigerator, ready for use.

The test tubes require a good deal of space on account of their relatively large size and number. This makes itself felt in the laboratory work, during storing in the refrigerator and incubator, storing and transport from producer to user. In addition, the racks require storing and cleaning.

The fermentation test described above can also be carried out by positioning prefabricated bodies carrying the various types of sugar in a known solid substrate in a dish or container. The indicator may be conveniently present in the sugar bodies, or, alternatively, it may, in known manner, have been added to the substrate in advance.

Before the bodies are positioned, the substrate surface in the dish is evenly inoculated all over with a suspension or broth containing a pure culture of the microorganism.

After the bodies have been introduced onto the surface of the substrate, the sugar—and the indicator if this has been added to the bodies—will diffuse out into the substate. This takes place relatively fast in the substrates normally used. As a result, a successful reaction will not occur if the sugar is applied via a paper disc into which it has been absorbed, or via a tablet into which the sugar has been mixed. The diffusion must be delayed or limited.

SUMMARY OF THE INVENTION

According to the invention, the substrate around the applied body is limited, so that the sugar diffusing out will remain inside a peripherally closed chamber or confined region and equalize itself there with an evenly distributed concentration. Thus, this final concentration is dependent upon the volume of substrate enclosed and upon the quantity of the sugar applied.

A more detailed description according to the invention, will be given hereafter. The limitation is achieved by means of supporting elements which encompass or confine a space closed laterally on all sides. The supporting elements are pressed down into the solid or semi-solid substrate, preferably so that their lower edges reach the bottom of the dish, while their upper edges preferably protrude somewhat above the surface of the substrate. In other words, the supporting element should preferably be somewhat higher than the depth of the substrate, which is generally about 0.5 cm or less. The diameter can be, for example, 0.5–1.5 cm or some other suitable size. The supporting elements may be open or closed at the top.

The supporting elements contain those types of sugar which are to take part in the reactions. Suitable concentrations and quantities of the sugars, for example, absorbed in filter paper or mixed into a suitable mass, are placed, during manufacture, in an expedient manner in the supporting elements. This can be achieved, for example, by means of a lining containing the sugar types and fixed to the inside of the walls of the supporting element. This lining may, if desired, rest on a lower inner shelf or step just above the lower edge of the supporting element. Alternatively, the sugars can be placed in hollows in the walls of the supporting element, in which case internal wall lamellae are perforated so that diffusion can take place into the space actually enclosed by the supporting element. The bottom of the wall cavity may conveniently consist of the solid lower edge portion of the supporting element.

In addition to the walls which surround the supporting element to carry the types of sugar, internal installations in the supporting element may also be used for the same purpose. Thus, in the center of the supporting element, there may be mounted a torpedo-, projectile- or star-shaped part, or other similar parts of expedient shape. They can be fixed, for example, by means of a supporting spider carried by the upper edges of the supporting element. Furthermore, the supporting element can have partition wall sections of various shapes which fully or partly subdivide the space which the supporting element actually surrounds. These partition walls, and in fact all internal installations, may, like the surrounding walls, be of hollow construction with perforated wall lamellae.

After a supporting element containing a sugar has been placed in the substrate, diffusion takes place in the part of the substrate enclosed by the walls of the supporting element. In the case of supporting elements with perforated internal wall lamellae, diffusion takes place through these holes.

The amount of sugar which in one or another of the methods mentioned is introduced together with the supporting elements during the production process, is so adjusted that after diffusion into the substrate bordered by the walls of the supporting element, the sugar will assume a concentration suitable for the fermentation tests to be carried out.

When carrying out fermentation tests, good results will be achieved irrespective of the geometrical form of the cross-section of the supporting element, but even though this is so, it may be of interest to discuss the shape of the supporting element in relation to diffusion equilibrium. The shape of the supporting element and the positioning of the sugar affects the rapidity with which the final concentration of the sugar is established in the substrate in the supporting element. A circular supporting element, with the sugar placed along the wall, surrounds a quantity of substrate which will be relatively slowly penetrated compared to non-circular shapes due to the fact that a circle has a relatively large area compared to its circumference. Placing the sugar in the middle of the round supporting element and/or along partition walls in addition to along the inner wall of the supporting element entails a more rapid state of diffusion equilibrium. Also, for example, a narrow rectangular supporting element, with the sugar placed along the walls, will be favorable for a relatively rapid establishment of the final sugar concentration in the substrate enclosed. With certain reactions other than fermentation tests, the choice of an expedient shape of supporting element may have practical consequences for the course and outcome of the reactions.

An actual or "positive" fermentation reaction is revealed by change of indicator color after incubation at 37° C. for a suitable period, while no or "negative" reaction is characterized by no change of color. The results of reactions are easy to read.

Gas production may be detected by development of air bubbles after inoculation into the depth of the substrate in the case of, for example, glucose as the active substance. In the case of a solid agar substrate, gas production will manifest itself by breaking up the substrate.

When it is desired to maintain anaerotic conditions during testing, the invention lends itself readily to such conditions by providing a sealing layer, for example, of paraffin at the top of the substrate within the supporting element by addition of the paraffin after the supporting element has been inserted into the substrate to the bottom of the container.

In a container containing a substrate, for example, a Petri dish, a number of supporting elements are placed at suitable mutual distances. Each supporting element contains one type of sugar, and thus all the supporting elements together represent the different types of sugar with which the fermentation test with the bacterium culture in question is to be made.

It is convenient to supply the supporting elements to the substrate from a dispenser similar to those normally used for positioning paper discs containing antibiotices. The supporting elements containing the sugars are stored under sterile conditions, stacked on top of one another in magazines, each magazine containing supporting elements having the same kind of sugar. In the dispenser or depositing device there is room for several magazines side by side, each magazine containing a different type of sugar.

Especially if delicate substances are contained in the supporting elements, it may be preferable to store them not only under sterile conditions in magazines, but also vacuum-packed.

After the supporting elements have been positioned on the surface of the solid substrate they may, by hand or machine, be pressed so that they penetrate the substrate and establish contact with the bottom of the dish, with the help of, for example, a plunger or similar device which presses down all the supporting elements in one and the same operation. The upper edge of the supporting elements, according to the invention, should preferably protrude somewhat above the surface of the substrate, so there is usually no danger of the surface of a plunger contacting the substrate.

If required, the supporting elements may be provided, at their lower edges, with small anchoring feet in order to prevent rebound from the surface of the substrate.

The supporting elements may be mounted in a supporting skeleton by means of which they can be simultaneously pressed to penetrate the substrate.

In accordance with the invention in U.S. Pat. No. 3,843,450, the supporting elements may be made to respond to magnetic forces or, in other words, they may be made magnetically responsive. By magnetic forces, they are attracted to penetrate the substrate and to make contact with the bottom of the dish. If required, the magnetic force may be applied after the supporting elements, by gravity, have landed on the surface of the substrate. The magnetizable parts can be placed, for example, inside the wall of the supporting element as its lower part or edge, and around the entire circumference. Alternatively, for example, the entire wall of the supporting element may be ferromagnetic. This material may conveniently have the form of an unbroken iron ring or sleeve, or also of granular parts, the maximum size being determined by the thickness of the tubular wall.

Below and along the upper, outer edge of the supporting elements, they may be provided with a collar of iron of suitable size and shape in order to increase the response of the supporting element to the magnetic field. If required, the collar may carry slim, downwardly projecting supporting studs extending outside the element and terminating flush with the bottom thereof. Their number may, for example, be four, and they may expediently be placed opposite one another so as to offer a balanced support.

It may be convenient to make the lower edge of the supporting element fairly sharp or bevelled so as to facilitate penetration of the supporting element through the substrate.

The supporting elements are discarded after use. Except for the above mentioned magnetizable components, they can, with advantage, be made of plastic or the like, which is destroyed by burning.

The sugar fermentation reactions are not critically dependent upon complete contact or sealing between the bottom of the dish and the lower edge of the supporting element.

Even a roughly cut lower edge of a supporting element ensures reactions of just as good quality as those with very good contact. Nevertheless it is possible, if desired, to establish adhesion between the lower edge and the bottom of the dish.

The identities of the reactions are determined automatically or semi-automatically in accordance with the invention described in U.S. Pat. No. 3,843,450 by means of defined positions.

Also the outcome of each reaction is a function which may be read by machine in accordance with U.S. Pat. No. 3,843,450. The readings are made as indicated in the patent, preferably under visual control. The data machine used indicates in a simple manner whether a reaction is positive or negative, or the degree of positivity shown by the reactions. In such a case as this, with clear, distinct color reactions and well defined criteria for determining the outcome of a reaction, it may, in accordance with the above mentioned patent, be possible to take the readings fully automatically.

Conventionally, when carrying out fermentation tests, one investigation is made for each type of sugar. A defined, convenient concentration of the sugar is used. Investigations carried out by the inventor indicate that it would be possible to achieve a better differentiated diagnostic expression if several concentrations of the particular sugar were used in the test. Such a method would be prohibitive with the working methods available by present day techniques. Even when only one concentration of each kind of sugar is used, fermentation tests impose a heavy load on the laboratories.

The invention, however, makes it possible in a simple and labor-saving way to carry out a fermentation test with several concentrations of one kind of sugar. Apart from using a separate supporting element for each sugar concentration, it is possible to use one supporting element for all concentrations, the supporting element being divided into separate chambers to carry the sugar concentrations. The supporting element may in such a case, for example, have the shape of a relatively long rectangular structure divided into consecutive transverse rectangular sections. Each section contains a given concentration of the sugar in such a way that there is a successive increase or decrease in the sugar concentration from section to section in the long rectangular supporting element. This supporting element represents therefore a particular type of sugar, and its sections, various concentrations of that sugar.

The type of sugar is identified by the position of the rectangular supporting element as such, and the concentration of sugar where a possible fermentation first occurs is determined by the position of the chamber concerned in the section row.

The supporting element under discussion may also be used with different types of sugar in the chambers.

However, as mentioned above, the invention is not restricted to use in fermentation tests, but is applicable to a large number of microbiological, serological, immunological, clinical-chemical and similar tests, where the reactivities of the various active substances and agents applied to the substrate, i.e., changes in growth and/or other reactions between the active substances and agents, are the subject of the investigations.

For example, the invention could be applicable to sensitivity determinations of bacteria towards antibiotics (and chemotherapeutics).

Today such determinations are usually made by means of discs containing antibiotics. A mechanical and automatic embodiment of this method is described in U.S. Pat. No. 2,843,450. The principle of the antibiotic disc method is to measure the diameter of the inhibition zone around the antibiotic disc and use this measurement as an expression of the sensitivity of the bacterium towards the antibiotic concerned, of which the disc contains a given amount.

In contrast to this, the present invention permits sensitivity determinations to be carried out in a simple manner by means of a titration technique. In this manner, a quantitative determination is achieved in terms of different concentrations of an antibiotic. In some cases this is more advantageous than the conventional method involving measuring the size of the zone diameter. The methods supplement one another.

According to the invention, supporting elements containing various concentrations of any antibiotic may be manufactured in advance for use in connection with the quantitative technique discussed above. In a titration test a given series of supporting elements is used for each antibiotic in such a way that the concentration of the antibiotic in question increases from one supporting element to the next. In addition to individual supporting elements, a supporting element subdivided into section chambers, as described above, can also be used for this purpose. The chambers have been supplied in advance with various concentrations of an antibiotic increasing in steps from chamber to chamber. Observations are made of the lowest concentration which inhibits growth, assuming that the bacterium being investigated is sensitive towards the antibiotic in question.

Today, if it is desired to carry out a quantitative sensitivity examination of the kind mentioned, this must be done in a series of test tubes containing broth, or in containers holding solid substrate, containing concentrations of antibiotic increasing in steps. On account of the labor this involves, this present-day technique would be prohibitive as a general routine method. Yet, in spite of the amount of work involved, it is used when determining the sensitivity of tubercle bacilli. This is due to special circumstances to be described below. The invention, however, makes it possible, in a simple manner, to make use of a titration technique for determining the sensitivity of tubercle bacilli.

The reason why sensitivity determinations of tubercle bacilli towards antibiotics differ from the sensitivity determinations of other bacteria, is the relatively very slow growth rate of tubercle bacilli. One consequence of this fact is that it is not convenient to determine the sensitivity of tubercle bacilli by the antibiotic disc method in the conventional manner.

However, the present invention makes it possible to determine the sensitivity of tubercle bacilli also by measuring the size of the zone inhibited. This can be achieved by using a relatively long and narrow rectangular supporting element as a support for an antibiotic. The antibiotic is fixed to the inside of one of the short sides of the supporting element. The diffusion of the antibiotic concerned is guided by the shape of the supporting element in a compressed volume along the longitudinal axis of the rectangular supporting element. The length of the zone inhibited is a measure of the sensitivity. The supporting elements may be open or closed at the top, the closure, when present, being in the form of a flat transparent roof. This cover will delay the desiccation of the substrate and reduce the risk of contamination during the incubation period of several weeks at 37° C. which is necessary for permitting the growth of the tubercle bacilli to develop. In itself, the sealing of the substrate dish is not entirely sufficient to afford protection against a certain degree of desiccation during such a long period of incubation. Additional sealing of the dishes is required (for example with tape) or they can be incubated inside plastic bags or boxes. These measures can be rendered unnecessary by using supporting elements closed at the top as mentioned above.

This invention also lends itself to an expedient application of a serological technique, particularly an immunodiffusion or precipitation technique. This very important technique has a multifarious and increasing application, but it is laborous and difficult to use in series tests. With the help of this invention, this technique will be made available in a great many fields for routine laboratory work and will, to a significant degree, contribute to increasing the breadth of information concerning laboratory investigation and research and to enhance their significance.

Instead of inoculating the substrate (preferably at the surface) with an agent consisting of a bacterium culture, it is possible, in this case, to spread a quantity of an agent consisting of antigen or antibody over the surface of the substrate, or mix it in with the substrate before pouring it into the dishes, all according to whether the supporting elements contain antibody or antigen respectively. When employing a quantitative precipitation technique, the prefabricated supporting elements contain graded quantities of the said substances.

It is only necessary for the substrate to be a nutrient when microbial growth is to take place. In addition to the compositions referred to earlier, it may be made on the basis of cellulose, starch or other suitable substances. A polyacrylamide gel may also be used. It is a transparent and inert gel, and it is possible to vary the concentration of acrylamide over a wide range in order to have gels of different porosity. Thus, larger pores are provided by lowering said concentration. The gel, as well as other gels, can in some instances with advantage be mixed with other gels, such as an agarose gel. The most common gel is an agar gel which possesses substantial strength even with very high water content. Agar is inert chemically and is suitable for examining diffusion tests. Agarose is a purer product than agar and gives more transparent gels. It has even a higher gel strength than agar. Lowering the concentration of agar and agarose and other gelling components as well, gives gels of larger porosity. In case of microbiological testing the substrate will contain a nutrient, although not necessarily so if the articles applied to the substrate serve as vehicles for the nutrient, such as growth requirements and growth promoting factors. Prior to inoculation, the substrate in microbiological testing should be sterile, although not necessarily strictly so if a relatively heavy inoculum is used in a relatively short incubation period.

Generally speaking the composition of the substrate shall consist of a material which permits diffusion and gives it a solid or semi-solid consistency. The latter is usually somewhat elastic, but it may also be plastic. Furthermore, the substrate must be penetrable by the supporting elements.

It has been reported by Hitchens in J. Inf. Dis. 29, 390, 1921 and by Falk et al. in J. Bact. 37, 121, 1939 that in the case of a number of different bacteria, anaerobes as well as aerobes, bacterial growth could be readily detected in semi-solid agar substrates. In fact, a more rapid and luxuriant growth was observed by using such semi-solid agar substrates than by using plain broths or solid agar substrates.

The substrate may be stratified, for example, having a solid agar as a bottom layer and a semi-solid agar as a top layer. In such a substrate the supporting elements will be kept in position by the side support provided by penetration into the solid agar, whereas the semi-solid agar will permit rapid diffusion and equilibrium of the active substances, and also more rapid and luxuriant growth.

In some cases, it may be sufficient to use supporting elements that are partially open laterally, for example, rectangular supporting elements from which the one short wall is missing, or which form open curves. Supporting elements of such a shape will constitute something between the fully open ones, known per se, for example, paper discs, and those described above which surround a space closed on all sides. The material which is to diffuse is fixed to the far wall of the supporting element, and the diffusion, in its first phase, is guided in a fixed direction by the walls of the supporting element. When the diffusion has extended beyond the bounds of the supporting element, it will spread in all directions.

The supporting elements may be of various shapes, each suited for specific diffusion experiments. This may apply to various immunodiffusion tests but is not limited to this particular application. Thus, it may be very useful to consider and make use of the same expedient when bacterial growth is involved in the experiments, for example, when testing synergism or antagonism between antibiotics towards bacteria. This investigation is an important supplement to the usual sensitivity determinations, and the possibility now available to include such tests in normal routine investigations is a large and important step forward.

The invention may also be used in connection with investigations involving growth factors. In advance, growth-promoting substances can be placed in the peripherally, for example, fully closed supporting elements. After placing the supporting elements in the inoculated substrate there will, through diffusion of the substances mentioned into the basic substrate in the dish, be produced new substrates in the various supporting elements, different from that originally present in them. These new substrates consist of the basic substrate and one or more additional different components all dependent on the number of growth-promoting substances placed in the supporting elements. The basic substrate in the container may be water, whereas dehydrated selective or differential substrates may be located or placed along or in the walls and/or internal installations of the supporting elements. Different substrates are thus produced in one dish by reconstitution. Observations are then made of the inoculated bacterium culture in the different supporting element to see whether they react with abundant, unchanged or possibly reduced growth, in response to the addition of the various substances. The technique may be used in connection with diagnosis or for purely experimental purposes.

The inhibitory effect of dyes and other inhibitory chemicals on bacteria are known from various studies. The invention makes it possible in a rapid and automatic way to use such dyes besides antibiotics and growth promoting substances making complex combinations of nutrients and chemicals to study the growth pattern or profile determination of bacteria to provide bacterial identification. Enzymatic profiles may also be used in such identification. Since the invention makes it possible to establish a primary noting by machine of bacteriological or other data in machine or on-line contact with a central data processing unit, the invention permits automatic computer assistance in handling the data concerning the wide range of biochemicals which may be involved in the "metabolic fingerprinting" and enzymatic profile identification of bacteria.

Reactions may be detected more readily and rapidly by applying a distinction promoting substance, such as a tetrazolium salt or dye to the reaction areas of the substrate. Thus, a tetrazolium indicator may be applied to the substrate prior to the outset of a test or during the first steps thereof which test may be, for example, determination of bacterial sensitivity to various antibiotics, or preferably said indicator may be applied after 6–7 hours incubation period permitting the results to be read shortly after (V. J. Boyle et al., Antimicrobial Agents and Chemotherapy, 3,418, 1973). The color development induced by the reduction of the indicator where growth occurs on the substrate, is readily detectable and causes delineation of distinct zones of inhibition even when growth is slight after the shortened period of incubation indicated above.

Some test methods require a secondary application, to the reaction region, of a particular substance (or substances) after a suitable period (or periods) in the course of the reaction, for example, after incubation for growth has taken place. Such a technique may be carried out by means of the invention. By using a dispenser, the secondary application can be made in the same pattern as the one used for the first positioning. For example, paper discs or other suitable bodies containing the substance or substances to be added, may be placed in the supporting elements. Another way of making secondary applications is to use a device having a number of inoculation points or pipettes arranged in the same pattern as that in which the supporting elements were placed.

This technique, characterized by the secondary application of substances after suitable periods of time have elapsed, may also be useful in the case of a quantitative method utilizing supporting elements which contain a substance present in a graded series of concentrations from one supporting element to the next. The possibility is thereby opened of adapting the method to different, relatively complicated titration techniques which today are carried out with liquid substances in test tubes. This also applies, for example, to reactions such as those in which red blood corpuscles are used to bring about haemolysis or haemagglutination as an aid to determining the titration end-points. Secondarily, the red corpuscles or other particulate material such as coated or sensitized latex particles or bacteria may be placed on the surface of the substrate within the supporting elements, where they will show very rapid and distinct agglutination in the case of serological testing, or they may have been admixed with the substrate in advance.

In some cases, the lining of the carrying body (or of the inner installation) may be bare i.e. lack any substance in which case the "secondary" application will in fact be the first contact of the active substance with the agent. The substrate may have a very simple composition. It may be adapted to existing requirements. The concentration of, for example, the agar may be made to suit prevailing conditions. It may, for example, be relatively low. The substrate may also contain substances other than the red corpuscles mentioned above, which take part in the reactions in constant quantities from reaction to reaction.

Alternatively, titration techniques may be employed by using the agents secondarily applied in graded concentrations, while the substances contained in the supporting elements in this case form a series with a constant concentration level.

Each supporting element need not contain only one substance, but may contain several. These substances may be pooled, or positioned separately at different and isolated places in the supporting element, in order to prevent a reaction from taking place between the substances before diffusion into the substrate.

The supporting elements may also be produced without substances being added during the manufacturing process, but with the possibility of adding required materials after the supporting elements have been placed in position in the substrate. With this object in view, the supporting elements may, for example, be supplied with a funnel-shaped input channel leading to a cavity in the wall of the supporting element where, in advance, a piece of absorbent paper may have been placed. These supporting elements too, may be of various shapes, each of a design suited for various specific diffusion experiments, for example, for examining precipitation patterns, testing synergism or antagonism between antibiotics, or when examining growth factors. They may enclose a hollow space peripherally closed on all sides, or they may be partly open. The purpose is to give research workers a technical aid that can improve possibilities and facilitate their work in the wide field of experiment covered by diffusion techniques and microbiology.

Furthermore, the invention makes it easy to determine the level of concentration of antibiotics in tissue liquids and to carry out other assays.

The invention may be used in a quantitative and automatic technique based on spectrophotometric readings through the contents within the positioned supporting elements. This may apply, for example, to clinical-chemical tests. The system may be used for carrying out autoanalyzer work. Depending on how many supporting elements are positioned by the dispenser at a time, the invention may easily be used in connection with a 12-channel run or more. The invention may, for example, be used for screening tests.

The system of the invention is very flexible in use. It may be used both with substances which disperse rapidly, and with those which diffuse slowly in the substrate selected. This opens great possibilities for many different reactions and types of reaction to be adapted to the technique thus providing the inherent advantages which will be discussed in more detail below.

The system of the invention utilizes principles which were defined and explained in U.S. Pat. No. 3,843,450. The advantages discussed in the said patent will also benefit the present invention. They are concerned with the automation of laboratory work and primary noting of data taking into consideration a technically desirable, or even necessary human and visual guidance and control. They are further concerned with the possibility of establishing direct contact with an electronic data processing unit with the enormous advantages offered thereby. Due to the present invention, these principles may find a more general and comprehensive application and will benefit a wide range of various microbiological, serological, immunological, clinical-chemical and similar tests and research in diffusion techniques in biological and chemical fields.

A technique adapted to the invention will benefit by advantages in addition to those mentioned above. These advantages relate partly to the actual laboratory work itself, partly to the preparation of the substrate, to cleaning, partly to questions of storage and transport and finally to safety aspects in the laboratory work concerned, in that the risks of errors and confusion are greatly reduced.

A more detailed explanation of these conditions will be given with reference to the technique used in the bacterial fermentation of sugars, mentioned above. The invention involves only one inoculation for the entire series of sugars, as opposed to the system in use today, which requires one inoculation for each type of sugar, or, in some cases, for two or three types. Furthermore, there is only one cover, namely the lid of the Petri dish, to take off and replace, as compared with the present practice of using a plug or cap for each broth test tube corresponding to the individual sugar types inoculated. In addition, all the fermentation reactions are collected in one handy, convenient and space-saving unit, the Petri dish, as compared with the present somewhat untidy, laborous and cumbersome system with all the individual broth test tubes to be handled and spread out one after the other in the holes of a rack. A further disadvantage in this connection is that the individual test tubes containing the various types of sugar are alike and can only be distinguished by means of a label indicating the type of sugar contained. Relatively speaking, the number of substrate dishes to be handled is small, and they are all of the same type, whereas the broth-containing test tubes are many, all externally the same, yet containing various types of sugar.

Whereas the reading and noting by the new technique may be carried out automatically under visual control or fully automatically according to U.S. Pat. No. 3,843,450, these operations are very laborious and time-consuming when conventional techniques are used, in which the various fermentation tubes, standing in close rows and columns in a rack arranged according to the kind of test and the type of sugar, have to be removed manually one by one for taking readings of the outcome and observing the identity, whereafter the data are noted by hand.

With the conventional technique, the risk of error is relatively large. This applies to the reading and noting of data. It also applies to the inoculation. This is repeated for every broth test tube in the series. It is possible to overlook a tube, or it may be inoculated from a loop which does not contain sufficient inoculate to promote growth. This leads to erroneous results.

Errors and confusion may also occur at an earlier stage. They may occur when the technical assistant fetches the test tubes containing the sugar broths. These are kept in a refrigerator and are grouped separately for each type of sugar. It may however happen that the test tubes that have not been used are put back in the refrigerator in a wrong group, inasmuch as the tubes in all groups have a similar outer appearance. Each test tube must therefore be checked.

Furthermore, errors and confusion may arise in the substrate department when the broths containing the various types of sugar are being prepared. Mistakes may also be made in affixing labels and when the tubes are transported to the refrigerator.

The fact already mentioned that a relatively large number of broths containing different sugars are required for fermentation tests, increases the possibility of error. This applies particularly when there are several specimens to be examined. In contrast to this, the technique according to the invention means that only a relatively small number of Petri dishes have to be handled, and all of the same type.

The invention will result in a considerable saving in space both during storage in the laboratory and during internal and external transport and dispatch. The small supporting elements can be housed in magazines as compact units as compared to the collection of relatively very large individual test tubes, which are awkward to handle. These require stands which take up a lot of space and have to be kept clean and free from contamination. Often the tubes are of glass, and must, after use, be put in an autoclave, washed and sterilized before they can be used again.

On the other hand, it is very simple, after use, to remove and destroy the Petri dishes and with them the supporting elements placed in the substrate. When removing them, it is of considerable advantage to be able to handle the small units, requiring little space, which the invention makes possible.

It is also very advantageous that the invention makes it possible to use a very simple and standardized substrate for various tests and experiments.

Although other modifications or versions of the fermentation test exist, none of them—or other laboratory methods currently in use or known—have any relation to the principles or system of the invention.

In the following, the invention will be described in more detail with reference to the drawings.

BRIEF DESCRIPTION OF DRAWINGS

FIG. 16 is a perspective view of a divided element and container prior to their engagement, FIG. 17 is a longitudinal section of the divided element and container subsequent to their engagement, FIG. 18 is a perspective view of a modified arrangement of the divided element and container prior to their engagement, FIG. 21 is a diagrammatic transverse sectional view showing apparatus for photometric analysis of the assembly shown in FIG. 20, FIG. 22 shows another embodiment similar to FIG. 18 of a modified divided element and container prior to their engagement.

DETAILED DESCRIPTION

The supporting element according to the invention may be used for many tests and experiments, but in the following description there is primarily given an account of the determination of bacteria on the basis of their fermenting effect on various types of sugar.

Figure 1:
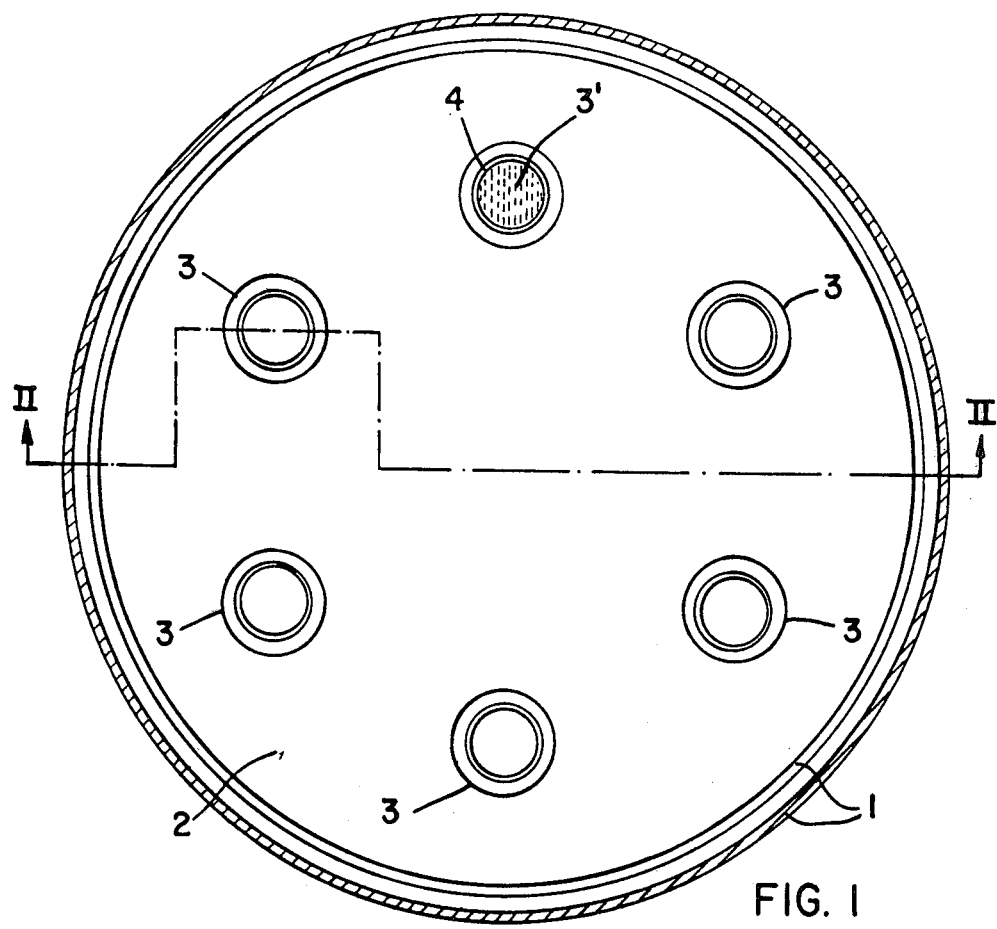
FIG. 1 shows a Petri dish containing substrate, seen from above and in section along the line I—I in FIG. 2, and provided with supporting elements according to the invention, for carrying out the experiments desired.
Figure 2:
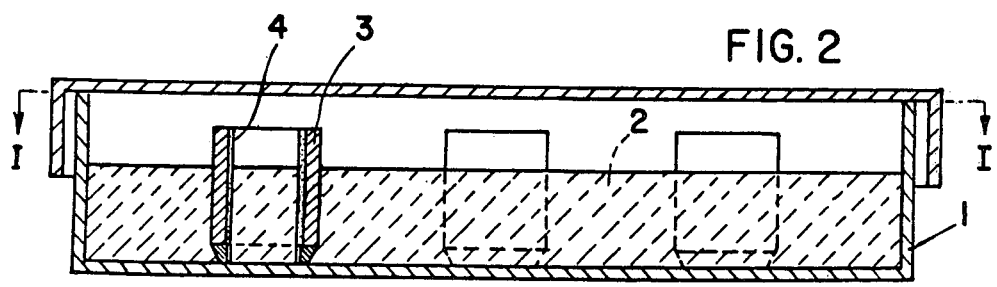
FIG. 2 is a view in cross-section along line II—II in FIG. 1.

The different sugars are added to a solid or semi-solid substrate, which is inoculated with the bacterium agent to be examined. The sugars are brought into contact with the substrate by means of a supporting element or carrying body according to the invention, for example, of the form shown in FIG. 3. The supporting element 3 in this embodiment is a tubular carrying body which has on the inside of the wall thereof a lining 4 containing a sugar (and an indicator if this is not contained in the substrate) to be used in the experiment. A ferromagnetic ring 5 is mounted at the bottom of the tubular supporting element. By means of one or more permanent-magnets or electromagnets, it is possible to draw the tubular supporting elements into position through the substrate in a Petri dish. This positioning is shown in FIGS. 1 and 2. Here, the Petri dish is indicated by numeral 1. The substrate which has been inoculated with the bacterium culture to be determined, is indicated at 2. Six tubular supporting elements of the type shown in FIG. 3 have been placed in the substrate. Each supporting element 3 has a lining 4 carrying its own type of sugar. This varies from one supporting element to the next in the substrate dish. The outcome of the fermentation reaction (which sugars, if any, are fermenting) is a diagnostic aid when determining the bacterium. Fermentation is revealed by a change in the indicator color. Such a change has been indicated in the substrate which is encompassed or confined by the supporting element designated at numeral 3' in FIG. 1. The fermentation causing the indicator to change color, is initiated after the various sugars and the indicator, if added to the bodies in the linings 4 of the six supporting elements have difused into the substrate enclosed by each individual supporting element, the diffusion of the sugar into the confined area producing an equilibrium concentration thereof in the confined area.

The lining 4 may, for example, be of paper or cellulose, and it rests, in this embodiment, on a step or shelf formed at the lower end of the tubular supporting element 3 by the ring 5.

Figure 4:
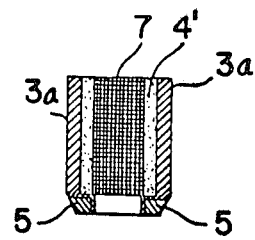
FIG. 4 is a vertical sectional view through another embodiment of the supporting element.

Instead of the lining, there may be provided a perforated wall lamella which forms the inner boundary of a cavity 4' in the wall of the tube 3a as shown in FIG. 4. The sugar is placed in the cavity. It is placed there either in its original form or it is absorbed in a lining or coating layer or mixed with an inert mass. It diffused through the perforated lamella and into the substrate encompassed by the tubular supporting element when this is pressed into the inoculated substrate.

The tubular supporing elements may consist of various suitable materials, for example, a plastic. The material may contain ferromagnetic material, either inserted or cast in position, or the supporting elements may be made of a ferromagnetic material, such as steel.

Figure 3:
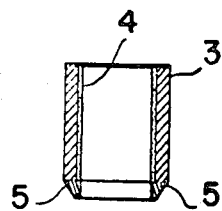
FIG. 3 is a vertical sectional view through one embodiment of a supporting element according to the invention.
Figure 5:
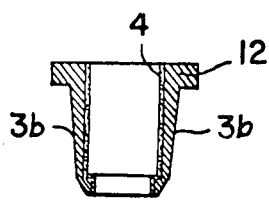
FIG. 5 is a vertical sectional view through another embodiment of the supporting element.
Figure 6:
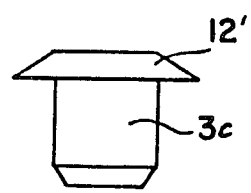
FIG. 6 is a side elevational view of another embodiment of the supporting element.
Figure 7:
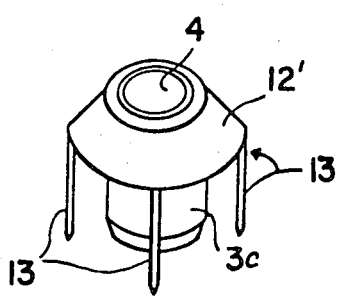
FIG. 7 is a top perspective view of another embodiment of the supporting element.

If, in special cases, more powerful magnetic forces are required than those obtainable by the ferromagnetic ring 5 in FIG. 3, (even when adding additional ferromagnetic material into the wall of the tube) the tubular supporting element may, as indicated at 3b in FIG. 5, have a ferromagnetic collar 12 or other suitably shaped member disposed around the upper end of the tube. In FIG. 5 the entire wall of the tubular supporting element, including the collar, consists of a ferromagnetic material. The supporting element has, in this case, a somewhat tapered shape as compared to the one shown in FIG. 3. In FIG. 6 the ferromagnetic collar 12' is of triangular cross-section disposed on a tubular supporting element 3c of the type shown, for example, at 3 in FIG. 3. Should it be necessary to make the supporting element more stable when it has a ferromagnetic collar at the upper end, the supporting element may be provided with four supporting legs 13 as shown in FIG. 7.

Figure 8:
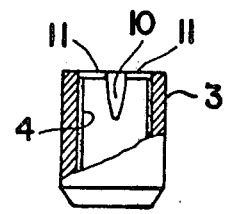
FIG. 8 is a side elevational view, partly broken away and in section, of another embodiment of the supporting element.

The embodiment in FIG. 8 has a projectile-like body 10 placed centrally in the tubular supporting element 3. This projectile-like body is supported from element 3 by a spider 11. The body 10 may be provided, on its outer face, with a coating containing the active, diffusible substance corresponding to that in the lining 4. In this manner, diffusion equilibrium in the substrate mass is rapidly achieved.

Alternatively, different diffusible substances may be used in lining 4 and on the surface of the body 10.

The body 10 may be hollow and perforated. The diffusible material may then be placed in the body either during the manufacturing process or at a later stage. The supporting elements intended for the latter purpose are manufactured without active materials in the bodies 10. These meet a demand in certain situations, for example, in certain experiments where the experimenter wishes himself to add the materials to be tested. This is achieved by allowing them to drip down into the hollow bodies.

Figure 9:
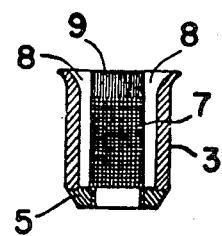
FIG. 9 is a vertical sectional view through another embodiment of the supporting element.

The supporting element as shown in FIG. 9 is suitable for experimental purposes connected with the same requirements for use as indicated above. The diffusible, active substance is allowed to drip down from above, into space or cavity 8, at the funnelshaped, widened part of the tubular supporting element 3. The substances diffuse into the substrate mass through a perforated inner part 7 of the supporting element, while a closed, upper part 9 prevents the substances from leaking out onto the surface of the substrate. In this way, the substances diffuse into the substrate along the wall of inner part 7.

Figure 10:
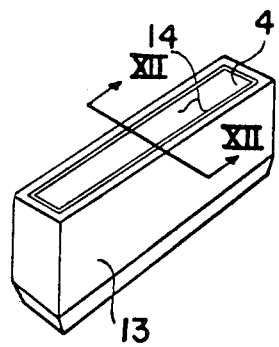
FIG. 10 is a top perspective view of another embodiment of the supporting element.
Figure 12:
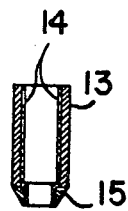
FIG. 12 is a section taken on line XII—XII in FIG. 10.

The term "tubular supporting elements" here also refers to supporting elements which are not of circular cylindrical shape, and for example, the supporting elements may be in the form of an elongated box, as shown at 13 in FIG. 10. Such a shape is suitable if it is required to guide the diffusion in a particular direction. This is achieved by placing the prepared lining 4 on one of the short walls as indicated in the figure. The diffusion will then spread along the body 13 of the supporting element towards the opposite short wall. If the linings are placed along one long side or along both sides as indicated at 14, diffusion equilibrium will be rapidly established. As shown in FIG. 12, the rectangular supporting element in FIG. 10 has neither base nor cover, and the supporting element may carry a ferromagnetic material as shown at ring 15. Further, the supporting element may be provided with a roof or cover, if desired.

Figure 11:
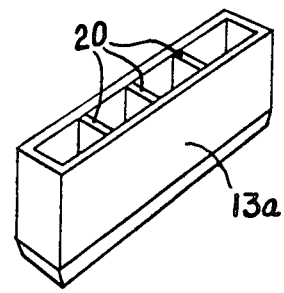
FIG. 11 is a top perspective view of another embodiment of the supporting element.

FIG. 11 shows a different embodiment of a supporting element 13a in the form of an elongated, rectangular structure, in which the interior space is divided by walls 20 into four equal spaces, each of which may have a lining containing a different substance. A section through FIG. 11 would have the same appearance as the one through FIG. 10 and shown in FIG. 12.

Figure 13:
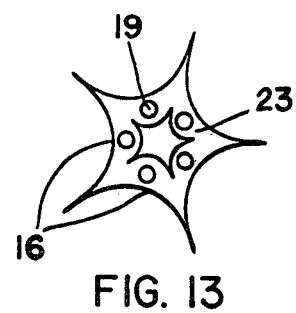
FIG. 13 is a top plan view of another embodiment of the supporting element.
Figure 14:
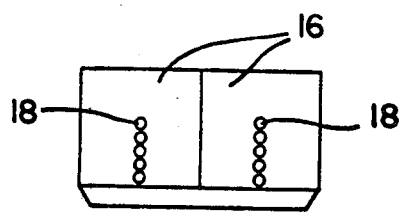
FIG. 14 is a side elevational view of the embodiment of FIG. 13.

In the embodiments shown, one of the objects of the invention is to keep the reaction confined to a certain area. According to the invention, the supporting elements, may, however, also be so designed that only the first stage of the diffusion is controlled and guided in a particular direction, while the final stage is free and unrestricted. An example of this is shown in FIGS. 13 and 14. In this case, the supporting element 23 is provided on its outer surface with longitudinal concavities 16 having small holes 18. These lead into longitudinal passages 19. These passages may either be furnished with active substances during manufacture, or the substances to be used or investigated may be added during the experiment. This can be achieved by depositing drops of the substances into the longitudinal passages 19.

The substances will, in time, diffuse out into the substrate through the holes 18. As the diffusion spreads further outwards, the direction will be determined by the shape and size of the curved part. It is not until a later stage, when the dispersal has proceeded beyond the confining borders, that it becomes uncontrolled in all directions.

As explained with reference to FIGS. 4 and 9, the supporting element may also be made with a perforated wall lamella confining a chamber into which the substances of interest may be introduced. Alternatively, the supporting element may be without chambers and perforations in the walls. In such a case, the substances in question may be added in the form of, for example, a paste in the longitudinal concavities 16, or they may be contained in a lining or coating layer which, in a suitable manner, is fixed to the outside of the supporting element.

The supporting element shown in FIG. 13 is hollow in the center. The supporting element may also be made without this cavity, but if so, it should be thin enough to ensure that it does not cause cracks to form in the surrounding substrate during or after its introduction.

Figure 15:
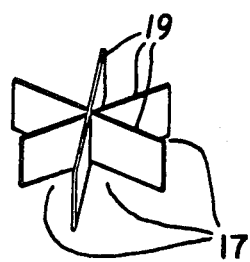
FIG. 15 is a top perspective view of another embodiment of the supporting element.

In FIG. 15, a star-shaped supporting element is shown wherein a plurality of flat walls 19 intersect along a common line. This supporting element also causes the substances to be diffused according to a fixed pattern. The substances in question are placed—or have already been placed—in the angles 17 formed between adjacent walls 19.

In FIG. 16 there is seen a supporting element 13a of the same contruction as shown in FIG. 11 positioned above a container 21 of conforming shape to that of element 13a. The element 21 contains a substrate 22 (FIG. 17) which may be liquid, semi-solid, or solid. The element 13a is insertable into the container 21 and into the substrate 22 therein as shown in FIG. 17. The lower edge of the element 13a forms a sealed relation with the bottom of the container 21 so that separate sections 23 of element 13a will form respective separate regions with isolated substrate portions in each of the regions when the element 13a is inserted into container 21 to the bottom thereof. A cover 27 can be placed on the assembly of the element 13a inserted into container 21 in order to cover the respective isolated sections.

Figure 20:
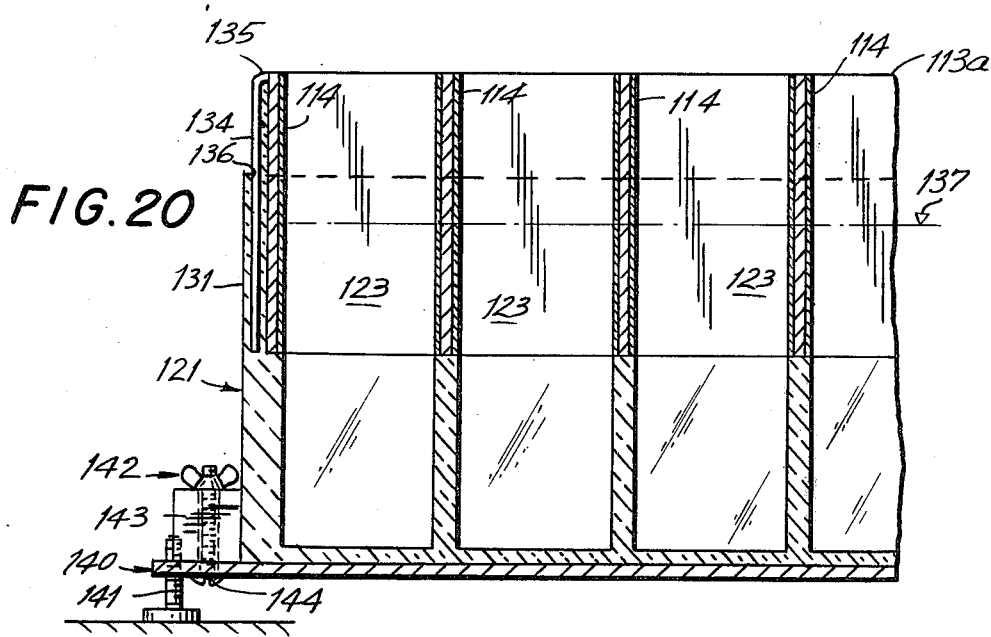
FIG. 20 shows the divided element and container of FIG. 19 in engaged relation.

FIG. 18 shows a somewhat similar arrangement wherein divided element 113a is insertable into container 121 as shown in FIG. 20 to form separate regions 123 corresponding to the number of divided sections within the divided element 113a.

The container 121 comprises upstanding walls 131 which form a shelf 132 against which the lower edge 133 of element 113a comes to rest when the element 113a is inserted into the container 121.

In order to guide the entry of the divided element 113a into the container 121, the element 113a is provided with two rectilinear guides 134 at one end and a single rectilinear guide 134 at the opposite end. The guides 134 are connected by webs 135 at the upper edge of the element 113a. The container 121 is provided with corresponding bores 136 in the opposite end walls therein to receive respective guide elements 134. The guides 134 and bores 136 are illustrated as being circular but obviously they can be of any suitable cross-sectional shape.

Beneath shelf 132, the container 121 is provided with a number of divided sections or compartments equal in number to the divided sections in body 113a. These divided sections or compartments come into registry with the divided sections of element 113a to form separate regions 123 with isolated substrate portions in each of the regions. The substrate is present in the container to the level as shown at 137. When the divided container 113a is inserted into the container 121, it penetrates into the substrate so that the lining of active material 114 which is on the walls of the divided element 113a become immersed into the substrate to enable diffusion to take place within the isolated sustrate portions in each of the regions.

The substrate can be liquid, semi-solid or solid. The substrate can be added to the container 121 immediately prior to the introduction of the element 113a therein or it can be previously provided in the container 121 and stored therein long before the introduction of the divided element. The agent can be inoculated or spread onto the surface of the substrate or throughout its entire content. The agent, such as colonies of bacterial cultures can be emulsified in a liquid substrate, such as water. The substrate containing the agent can also be body fluid such as serum or urine. Indeed, in some cases the substrate may, in fact, reveal with the subsequent examination with the active substance, that no agent is present.

Figure 19:
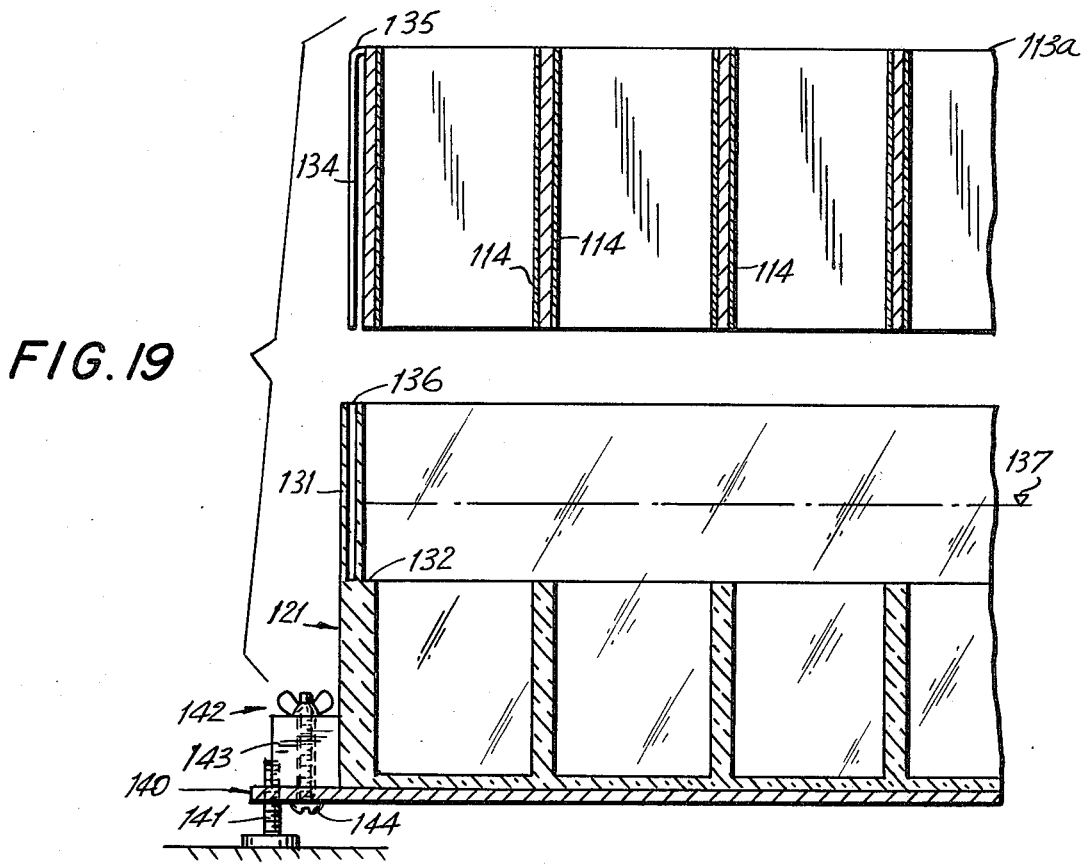
FIG. 19 is a sectional view of a portion of the divided element and container in FIG. 18.

The container 121 can be supported on a base 140 which is provided with leveling feet 141 at the four corners thereof to ensure a perfectly level condition for the substrate. A suitable means 142 is employed to hold the container 121 on the base and as shown in FIGS. 18 and 19, the holding means 142 comprises blocks 143 capable of engaging end walls of container 121 in clamped relation. Each block is traversed by a bolt 144 which rides in a slot 145 provided at a respective end of base 140. In operation, one end of the container 121 is brought to bear against a secured block 143 and the block at the other end is thereafter brought into clamping contact with the other end wall of the container 121 whereafter the bolt 144 is tightened to securely hold the container between the blocks. Alternatively, the clamping means can be in the form of a snap-lock or a spring latch or any other suitable quick release means.

The walls 131 of the container 121 terminate at edges 150 along the longitudinal sides so as to leave the depending chambers exposed as seen in FIG. 18. The chambers are formed of a transparent or translucent material in order to enable photometric analysis of the results which take place within the chambers.

The system for undertaking photometric analysis will be best seen from an examination of FIG. 21 wherein a conventional photometric analyzer is illustrated. Herein, light from a source 201 is directed into a chamber in the container 121 and due to the presence, for example, of a suspension therein due to reaction between the agent in the substrate and the active substance diffused from the walls of element 113a, the beam of light from the light source is scattered and its measurement can be taken as a measurement of the reaction e.g. the bacterial population in the case of a microbiological examination. The scattered light is measured at an angle with respect to the original direction of the light beam by a photosensor 202. A collimator 203 can be interposed between the container 121 and the photosensor 202. It is to be understood that all of the chambers can be examined by respective photometric analyzers simultaneously, or by a single photosensor through the medium of a relative movement between said photosensor and the divided container. If the reaction takes place at the surface of the substrate, the light source is directed through the container 121 to the surface of the substrate and the photosensor and collimator are positioned to receive scattered light. Other optical examination systems are known in the art and can be employed instead of the light scatter technique as described above. By way of example, spectrophotometric, optical densitiy measurement apparatus or other turbiodometric or nephelometric or radiation detection means can be used.

To one of the chambers in the divided container, no active substance should be added, for example, no antibiotic, since this chamber shall serve as a control chamber or reference or blank in the photometric measurement. The use of a reference chamber is applicable to all embodiments when a plurality of separate sections with isolated substrate portions is formed. Thereby, the degree of reaction of the agent with active substances can be referred to a common basis, i.e., the reference chamber where no reaction takes place.

Since it is common in microbiological testing procedures to shake the container to ensure proper suspension of the agent and rapid elution of the active substance, any suitable means can be employed for agitating the container 121 after insertion of the divided element 113a into said container.

It is also well known to incubate the substrate to promote the reactivity of the agent and active substance(s), i.e., changes in growth and/or other reactions between the agent and active substance(s), in many testing procedures and for this purpose the container 121 and the inserted elements 113a can be placed into an incubator prior to photometric analysis. The incubator may include an agitator means to effect agitation of the assembly in the course of incubation.

The level of the substrate which has been shown at 137 can be visually determined by the provision of level indicator markings engraved in each end wall of the container 121. The indicator markings may be arranged in opposite pairs, each pair being optionally given a different color. The markings not only serve to indicate the quantity of liquid contained in the container 121 but also to aid in leveling the container for uniform distribution of the substrate in each of the chambers in the container and in the corresponding sections of the divided element 113a inserted into the container.

With the above construction there is only a minimal risk of cross-contamination of active substances, eluted from the separate sections of the divided elements, among the isolated liquid substrate portions in the separate regions when the divided element is inserted into the container. In this respect, the insertion of the divided element into the container will be quickly completed which will leave too short a time for any cross-contamination. Nevertheless, in order to reduce even further, any risk of such cross-contamination, the level of the upper surface of the liquid substrate may be kept just above the shelf at the top of the divided sections or compartments in the lower part of the container.

Figure 23:
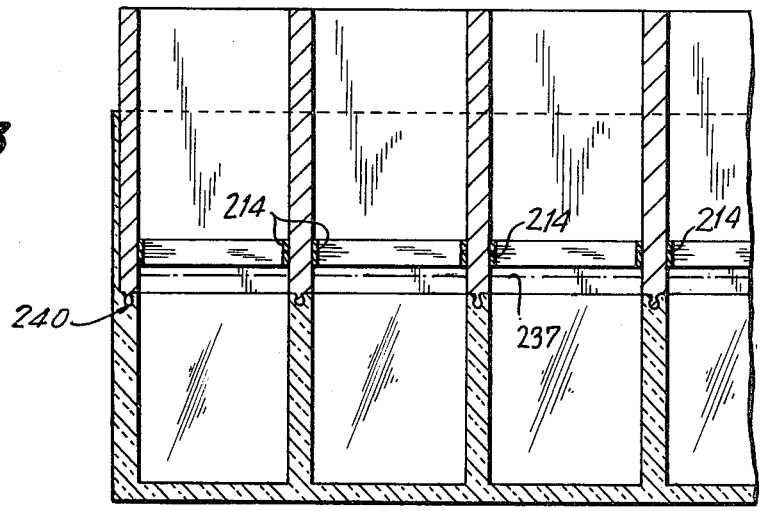
FIG. 23 is a sectional view of the divided element and container in FIG. 22 in engaged relation.

In order to physically safeguard against any possibility of cross-contamination, the construction as shown in FIGS. 22 and 23 is employed. Therein the lining 214 containing active substance is placed horizontally around the inside walls of each divided section 223 of the divided element 213a at a distance above the lower edge 224 of each section, so that the lower edge of the strip 214 will just avoid contact with the substrate surface 237 when the divided element 213a and the container 221 are joined. If desirable the lining may extend to the top of section 223. In stead of being placed horizontally, a strip may be placed vertically or in any suitable position on the inside walls of section 223. Furthermore, the lining may take any suitable form.

An appropriate agitation will then cause the liquid or semi-solid substrate to wash over the strip or lining and elute the active substance therefrom.

In order to provide a fluid-tight engagement of the element 213a with the container 221, an engagement means 240 (FIG. 23) is provided. The engagement means 240 comprises a continuous bead 241 which extends along the lower edge of the element 213a and which fits into a corresponding slot 242 extending along shelf 232 on which the element 213a rests when inserted within the container. As seen in FIG. 23, the bead is of circular section and is deformable in order to be snapped into the slot 242 for tight engagement therewith. As a result of the sealed engagement of element 213a with container 221, the lining strip 214 in each section 223 will be confined to act with the substrate associated with the respective chamber 225.

Figure 24:
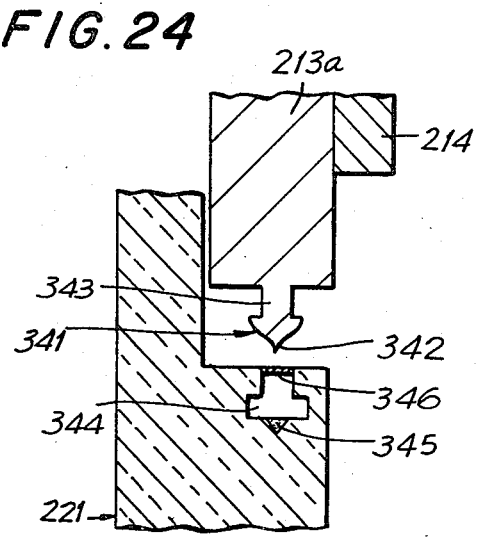
FIG. 24 is an enlarged view of a portion of the element and container of FIG. 22 prior to engagement showing a modified sealing means therefor.
Figure 25:
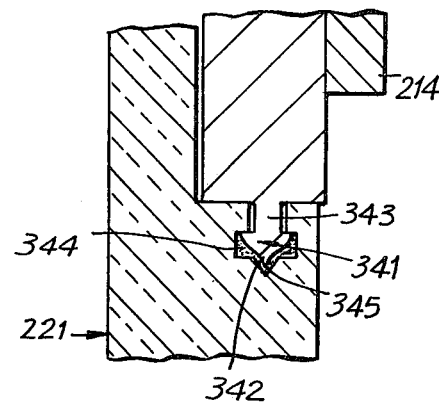
FIG. 25 shows the engaged relation of the divided element and container in FIG. 24.

FIGS. 24 and 25 show a modified form of engagement means particularly adapted to sealably engage the lower edge of the divided element with the container. In the embodiment in FIGS. 24 and 25, the bead 341 is shaped as a portion of a circle in cross-section with a sharp tip 342. The bead is connected by a neck portion 343 to the lower edge of the divided element. The bead is engagable in the slot 344 in the container by a snap effect, the tip 342 on the bead fitting into a V-shaped groove 345 at the bottom of slot 344. The groove 345 is filled with adhesive. The slot 344 is covered with a foil 346 or other liquid-tight cover. Upon assembly of the divided element and the container, the tip 342 of the bead will pierce the foil 346 and the bead will penetrate into the slot so that the adhesive in groove 345 will bond the lower portion of the bead 341 in the slot 344 to provide a liquid-tight adhesive sealing in addition to the mechanical snap-lock effect. The ruptured foil 346 will also act to prevent seepage of the substrate into the slot during the assembly operation.

Figure 26:
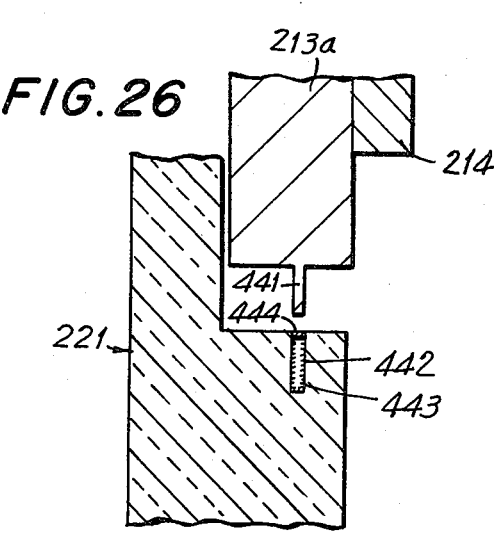
FIG. 26 shows a further modified arrangement of the sealing means prior to engagement of the elements.
Figure 27:
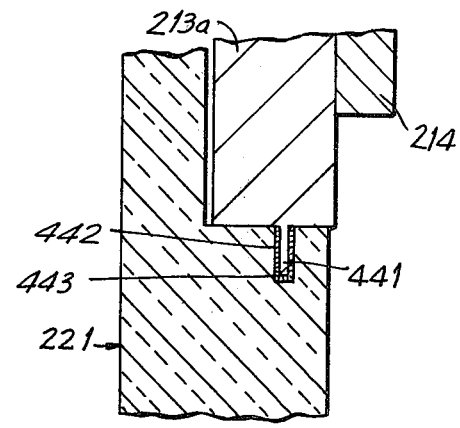
FIG. 27 shows the assembly in FIG. 26 after engagement of the elements.

FIGS. 26 and 27 show another embodiment of a sealing arrangement between the divided element 213a and the container 221 wherein the bead is in the shape of a rectangular projection 441 which fits into a corresponding rectangular slot 442 in the container 221. The walls of the slot are covered by a layer of adhesive material 443 to effectively bond the projection to the walls of the slot after assembly of the divided element and the container. A liquid-tight foil 444 is provided at the top of the slot.

Figure 28:
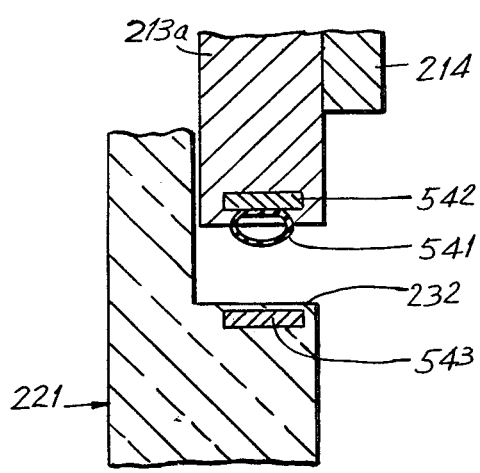
FIG. 28 shows an arrangement similar to FIG. 26 with a still further modified sealing means.
Figure 29:
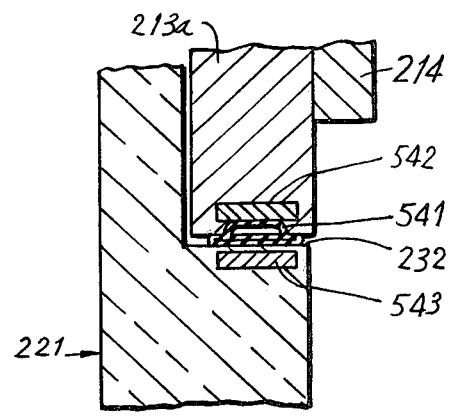
FIG. 29 shows the elements of FIG. 28 after assembly.

FIGS. 28 and 29 show a further embodiment of a sealing arrangement wherein a gasket or sealing strip 541 extends along the lower edges of the walls of the element 213a. As seen in FIG. 28, prior to assembly, the sealing strip 541 has an annular cross-section. After assembly, as shown in FIG. 29, the sealing strip 541 has been pressed into sealing engagement with the shelf 232 of container 221 whereby the sealing strip is deformed. The element 213a is forcibly engaged with the container 221 by magnetic effect produced by the use of strips 542,543, one of which is of permanent magnetic material and the other of magnetically responsive material, the strips being in proximity with the lower edge of element 213a and the surface of shelf 232.

Figure 30:
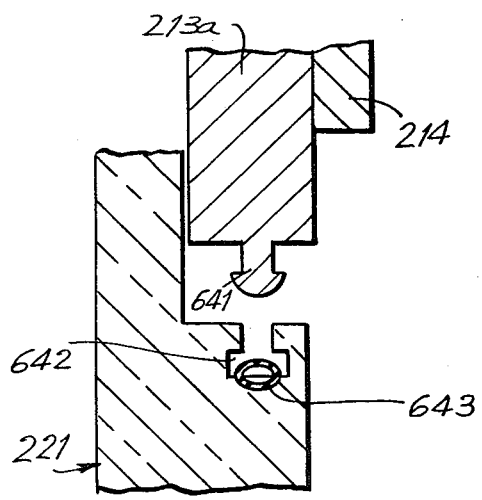
FIG. 30 shows another modified arrangement of the sealing means.
Figure 31:
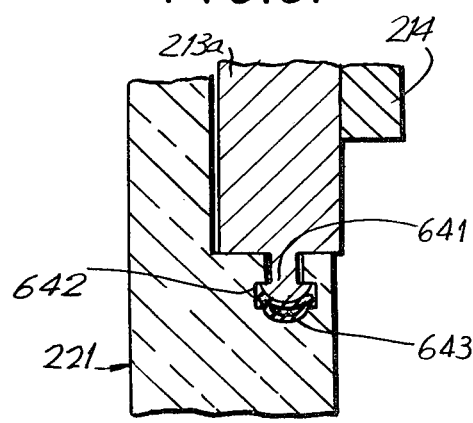
FIG. 31 shows the arrangement of FIG. 30 after assembly of the elements.

FIGS. 30 and 31 show another modified form of the sealing arrangement between element 213a and container 221 wherein the bead 641 has an enlarged head which is deformingly inserted into slot 642 in the container 221. The engagement of the bead into the slot is by snap-fit and at the bottom of the slot there is provided a resilient sealing strip 643 which is deformed by the enlarged head of bead 641 when the bead is inserted into the slot as shown in FIG. 31.

Figure 32:
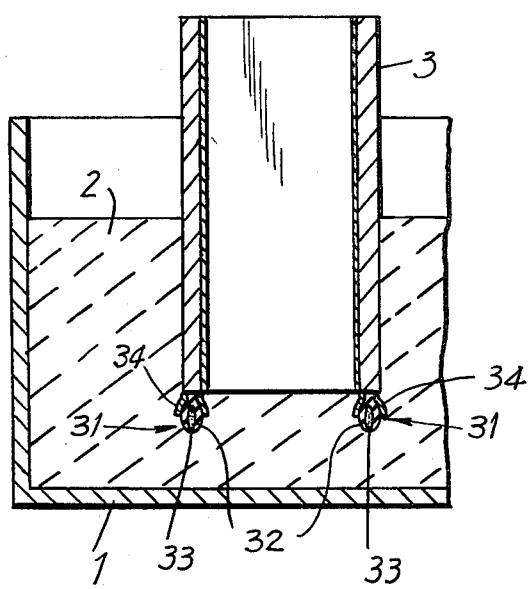
FIG. 32 is a sectional view showing a carrying element with sealing means therefor in a position prior to engagement of the carrying element with the bottom of the container.
Figure 33:
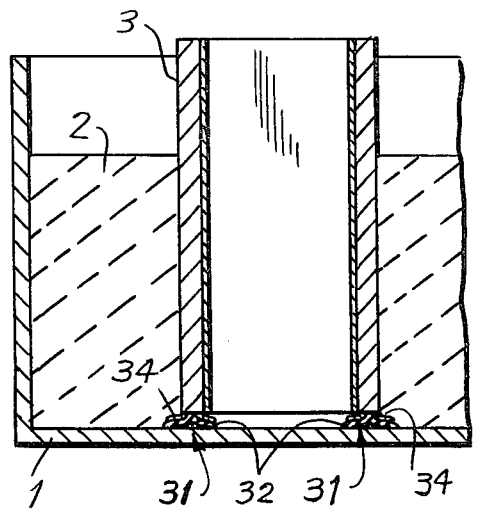
FIG. 33 shows the carrying element in sealed engagement with the bottom of the container.

FIGS. 32 and 33 show the provision of a sealing means 31 at the lower edge of an individual supporting element 3 for sealably engaging the supporting element in liquid-tight manner with the bottom of the container 1. The sealing means 31 is in the form of a suction-cup bead 32 of flexible material which, when brought into contact with the bottom of the container forms a sealed connection therewith in the nature of a suction cup connection. In order to promote the liquid-tight sealed relation between the suction-cup bead 32 and the bottom of the container, an adhesive 33 can be incorporated in a hollow in the suction cup bead 32. This embodiment is particularly effective when the substrate is a liquid or semi-solid and the container has a flat bottom. The bead 32 has an initially tapered, streamlined shape to facilitate its penetration into the substrate and to protect the adhesive 33 in the hollow. The bead 32 is provided with external reinforcements 34 extending along the lateral sides partially along the depth of the beads to give the beads sufficient support to resist the pressure due to the penetration into the substrate but which are yieldable when the beads 32 are urged against the bottom of the container and undergo deformation as shown in FIG. 33.

Although the sealing means 31 has been illustrated in conjunction with elements 3 they can also be effectively employed at the lower edge of the elements as shown in FIGS. 10–15.

Figure 34:
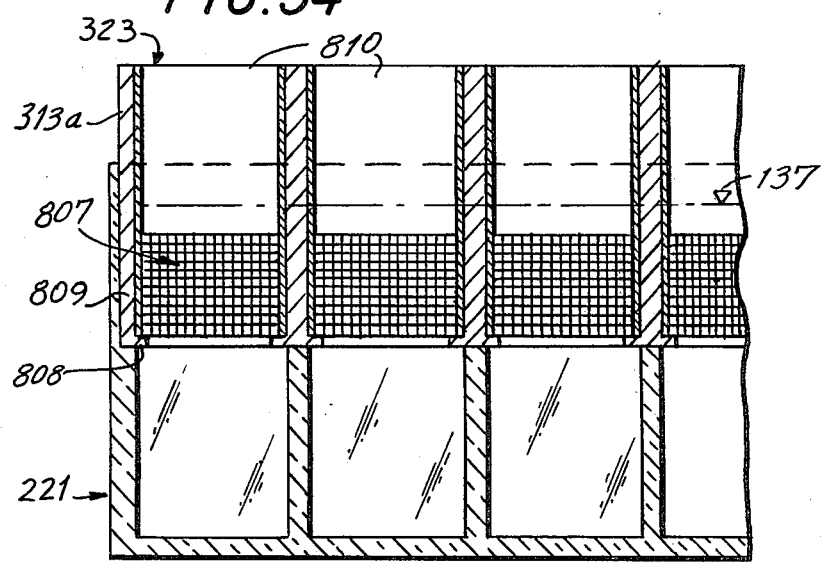
FIG. 34 is a sectional view of another embodiment of the carrying element engaged with the container.

FIG. 34 shows an arrangement wherein the divided element 313a has each of the sections 323 thereof constructed in the manner as shown in FIG. 9 wherein a perforated inner element or lamella 807 is mounted in spaced relation from the inner wall of the respective section 323. Each perforated element 807 rests on a step or shelf 808 formed at the lower edge of the section 323 and defines together with the walls of the chamber a cavity 809 in which active substance is placed. The active substance may be directly introduced into the cavity, for example, in the form of a liquid into a blank lining within the cavity or the active substance can already be contained within the lining. The top of the perforated element 807 is closed by a closed upper part 810 which prevents the substances from leaking out onto the surface of the substrate. The depth of the closed upper part 810 will be sufficient to penetrate into the upper surface 137 of the substrate in the container 221. Although no sealing arrangement has been shown in FIG. 34, it will be appreciated that any of the sealing and clamping arrangements previously described can be employed herein.

Figure 35:
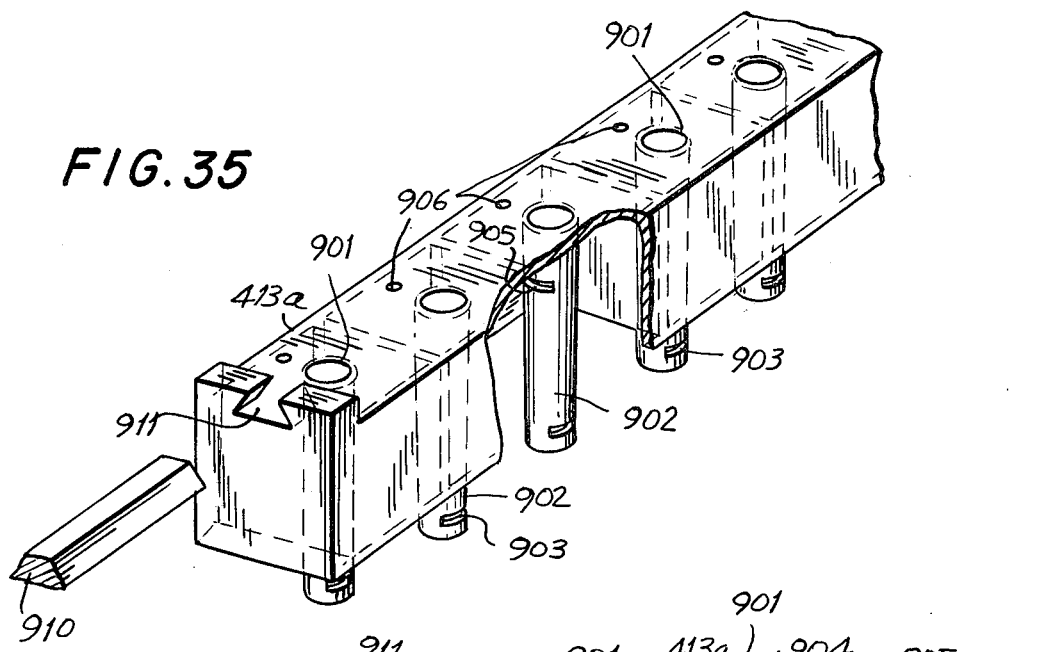
FIG. 35 is a perspective view, partially broken away, of a modified embodiment of the carrying element.

FIG. 35 shows a modified arrangement of the divided element 413a. The element 413a is in the form of a divided body as before with the exception that the divided sections are closed at the top wall except for openings 901 which lead into the interior of respective hollow inner members 902 which are integral with element 413a and which protrude beyond the lower edge thereof. When the divided element 413a is assembled with the container 221, the hollow inner members 902 project into the individual chambers 225 in the container 221 by penetrating into the substrate in the container 221.

The hollow inner members 902 are closed at the bottom and are provided in the vicinity thereof with openings or perforations 903 so as to allow active material which is housed in or added to each of the inner members to diffuse into the confined substrate in each chamber 225.

In order to prevent build-up of pressure in the hollow inner members 902 or in chambers 904 at the top of the separate sections in the divided element 413a when the divided element is inserted into the substrate in the container 221, each hollow inner member 902 is provided with a slot or perforations 905 near the upper end thereof to provide communication between the interior of the hollow inner member and the respective chamber 904 and in the top wall of the divided element 413a there are provided a number of vent holes 906 providing communication between the ambient atmosphere and the chambers 904.

The upper openings 901 of the hollow inner members 902 are aligned and may be closed by a narrow lid or cover 910 which is slidably engageable in gripped manner with a dovetail slot 911 in the divided body 413a to cover all of the openings 901. A corresponding dovetail slot 911 may be provided at the opposite end of the element 413a for receiving the remote end of the cover 910.

The vent holes 906 may be covered by a hinged cover or other suitable valve means for maintaining a closed condition within the divided sections in the element 413a until such time as a pressure build-up in chambers 904 causes the valve means to open.

Figure 37:
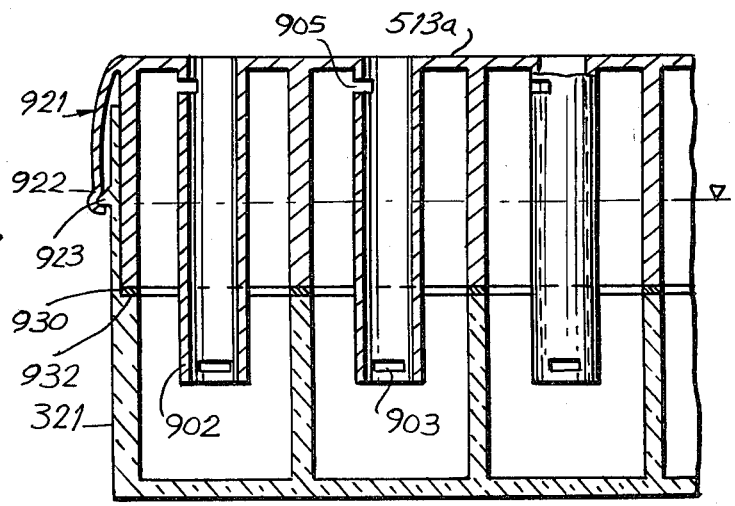
FIG. 37 shows a modified arrangement of the assembly as shown in FIG. 36.

FIG. 37 shows the provision of a combined locking and sealing arrangement for the assembly of divided element 413a and container 221.

The combined locking and sealing arrangement comprises an integral cover 921 formed at the top of element 513a which includes a depending leg 922 extending below the upper edge of the end walls of the container 321 when the divided element 513a and the container 321 are interengaged. The container 321 is provided with a transverse projection 923 which becomes engaged with leg 922 when the divided element 513a is engaged with the container. The leg 922 is deflected laterally when the element 513a is inserted into the container and it undergoes a snap-type action for engaging the projection 923 after the divided element 513a has been fully engaged within the container 321. Sealing strips 930 are mounted at the bottom edge of the divided element 513a for being simultaneously compressed against the shelf 932 on the container 321 and the sealing action is maintained by the pressure exerted by the engagement of leg 922 with the projection 923 after the divided element 513a has been fully inserted into the container 321.

Although the particular locking and sealing arrangement has been shown in conjunction with the divided element having hollow inner members 902, it is to be understood that the divided element may be of the form and construction as shown in any of the previous embodiments.

Figure 38:
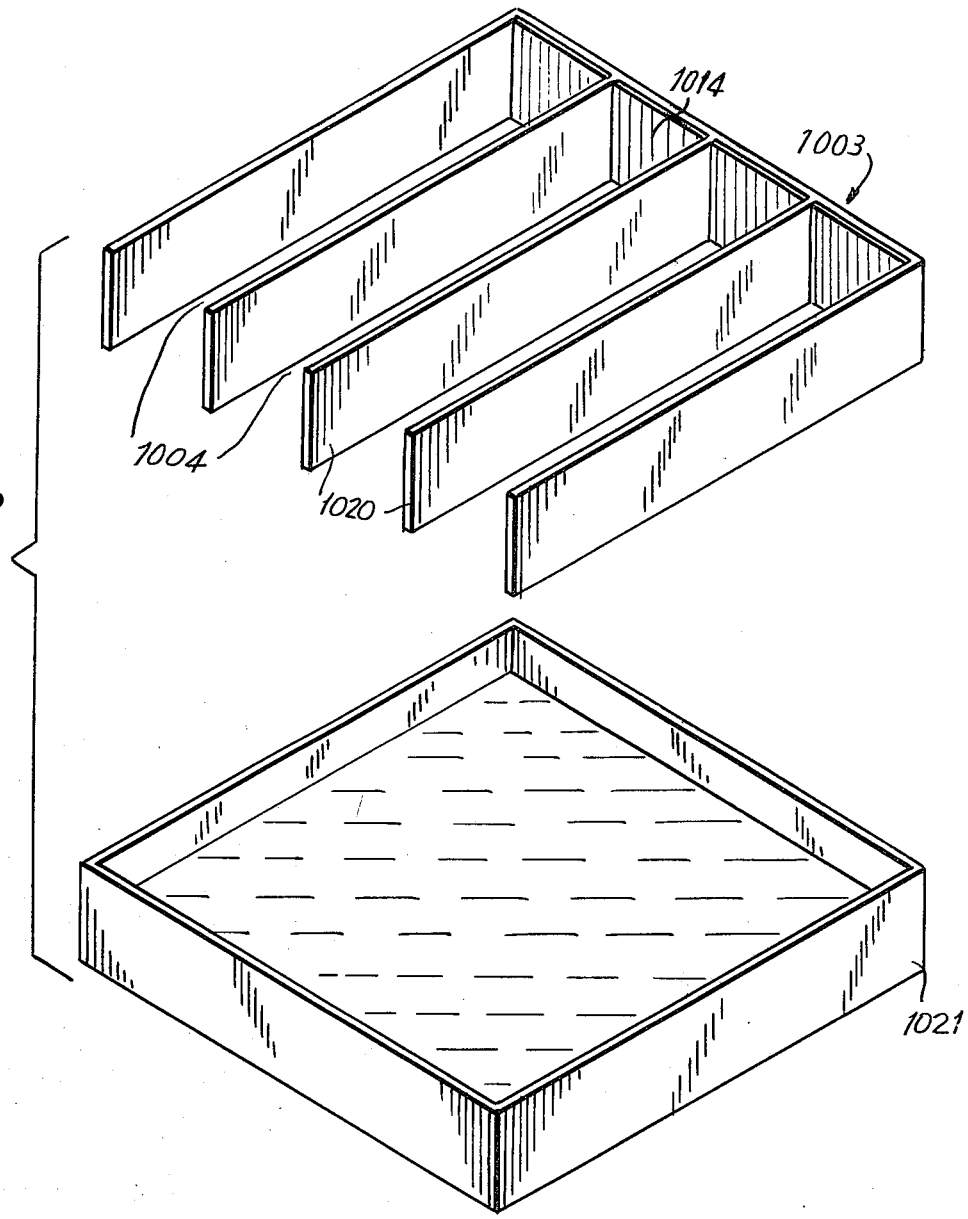
FIG. 38 is a perspective view showing a further modified divided element in separated relation with a container therefor.

FIG. 38 shows an arrangement wherein the reactivity of the agent and active substance can be determined by measuring a reaction zone. Specifically, in FIG. 38 the divided element 1003 is essentially constituted by a plurality of juxtaposed elements of the type as shown in FIG. 10. In this embodiment each of the divided sections 1004 formed in the divided element 1003 is provided with a lining 1014 along only one of the narrow end walls. When the divided element 1003 is introduced into the container so that the active substance in the lining 1014 on the end wall can diffuse into the substrate, the reaction takes place within each of the sections 1004 confined between relatively long walls 1020. These sections are relatively long and narrow rectangles and the diffusion of the active substance is guided by the shape of the sections 1004 along the longitudinal axis of the rectangular section. The length of the reaction zone is indicative of the degree of reaction between the active substance and the agent. Instead of the provision of lining 1014 on the narrow end wall, the active substance, for example, a liquid can be added by using a perforated lamella as shown by way of example in FIGS. 4 and 9, or an article containing active substance may be placed on or in the substrate close to the narrow end wall which in this case is devoid of active substance. The article may be a disc. The opposite narrow end walls of the divided element 1003 may be omitted.

Figure 39:
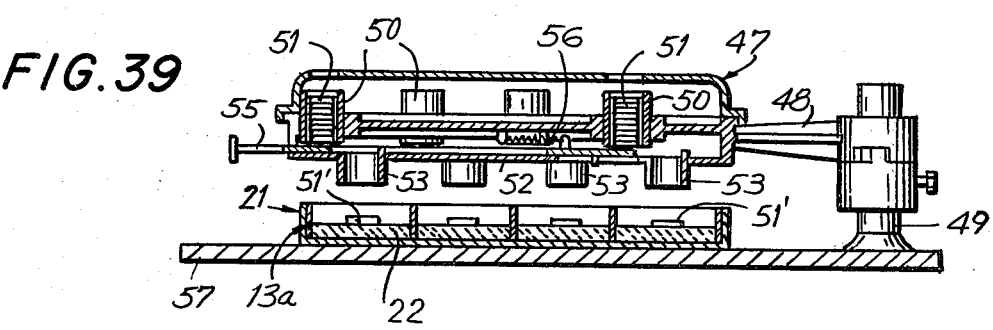
FIG. 39 is a sectional view of a dispenser in combination with an assembled divided body and container.

FIG. 39 shows a dispenser 47, for example, of paper discs 51 or tablets or other suitable bodies containing substances to be added to the substrate, in combination with the divided element 13a and container 21 of FIGS. 16 and 17. The discs 51 can be used to supply active substance in conjunction with the supply of active substance from the linings on the walls of the divided element 13a or in replacement of the supply of active substance from the linings on the divided element. In the latter case, the linings may be retained but will be bare or the linings can be omitted. Also, instead of linings, when used, on the walls of the divided element, a distributing means of the type as shown in FIGS. 4 and 9 can be employed. Additionally, the dispenser 47 can be employed with the embodiment shown in FIGS. 35–37 in which case the discs 51 will be deposited into the hollow bodies 902 and supported therein. A base 57 is shown for centering and supporting container 21 containing substrate 22. The dispenser 47 is supported by means of an arm 48 on an upright 49 on the base 57 for pivotal movement in a horizontal plane from the illustrated active position, which is determined by a stop, to an inactive position where the container can be inserted and removed. The dispenser 47 contains vertical dispensing tubes 50 adapted to hold stacks of discs 51. The stacks of discs normally rest on a base plate 52, which is fitted with outlets 53 laterally displaced in relation to the relevant dispensing tube 50. The bottom disc in each stack is moved to the associated aperture by moving a pusher 55 against the bias of a return spring 56. The pusher 55 is provided with a straight translational guiding support.

The base 57 and the dispenser 47 can be aligned with one another such that the outlets 53 in the operating positions are directly above the open upper ends of the sections 23 of the divided element 13a. Each set of discs released will fall parallel from the outlets 53 and be positioned on the substrate 22 as shown at 51' in FIG. 39.

It is also possible within the scope of the invention to employ a magazine containing the supporting elements in a dispenser similar to dispenser 47 and to provide means for mechanically and/or magnetically pressing the supporting elements into the container with the substrate. It is to be understood that the supporting elements and the conforming containers may be made relatively small in size so that a miniaturized system may be provided, although any appropriate size may be used.

Figure 36:
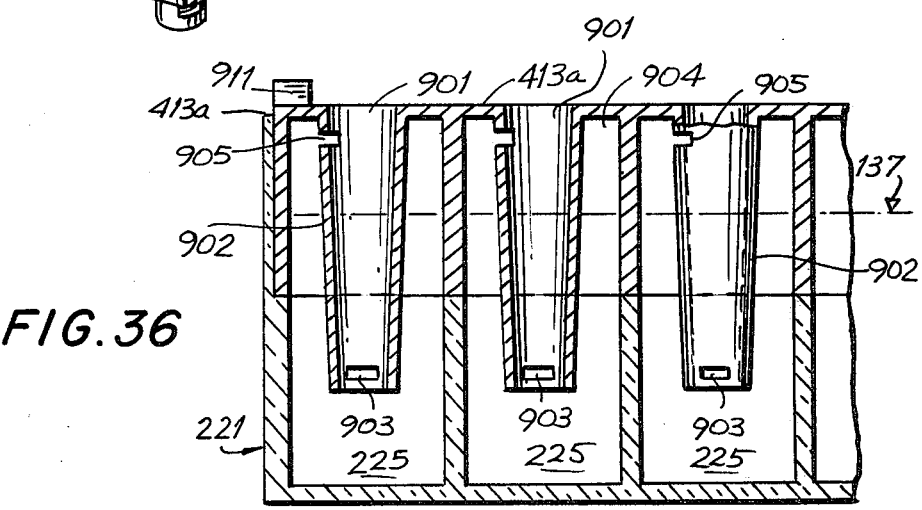
FIG. 36 is a longitudinal sectional view through a portion of the divided element of an assembly including FIG. 35.

Although, FIG. 39 has been described in conjunction with deposit of the discs onto the substrate after the assembly of the divided element and the container, it is possible in accordance with the invention to add the discs to the divided element into the hollow bodies 900 of the divided element 413a in FIGS. 35–37 or into cavity 809 of FIG. 34 before the divided element is inserted into the container, although such additions by means of a dispenser should preferably be made after assembly.

The container can be provided with a flap or other suitable attachment (not shown) on which identification and information data can be provided in accordance, for example, with the sample and person from which the agent added to the substrate is derived and with the test involved. The principles disclosed in U.S. Pat. No. 3,975,716 may be used for data identification and information in this respect.

The disclosed embodiments merely serve to illustrate the invention and not to limit it, inasmuch as variations and modifications will become apparent which will fall within the scope of the invention as defined in the appended claims.

What is claimed is:

1. Apparatus for carrying out biological and chemical diffusion tests in microbiological, serological, immunological, and clinical-chemical work, in which at least one active substance is contacted with a substrate containing an agent, the reactivity of the agent and active substance being the subject of investigation, said apparatus comprising a container containing the substrate, a divided carrying body with respective separated sections in sealed contact within the container such that the sections form separate regions with isolated substrate portions in each of said regions, said carrying body penetrating into said substrate in each of said regions and means supported by said carrying body for introducing said active substance into respective isolated substrate portions where the carrying body penetrates into the substrate by discharging said active substance into the penetrated substrate portions by diffusion whereby the action in said substrate is restricted to said separate regions.

2. Apparatus as claimed in claim 1 wherein said carrying body has lower edges and is in sealed contact with the container at said lower edges.

3. Apparatus as claimed in claim 2 comprising sealing means for forming a liquid-tight seal between the lower edges of the carrying body and said container.

4. Apparatus as claimed in claim 1 wherein said means for introducing active substance into the isolated substrate portions comprises an inner body supported within each section of the carrier body.

5. Apparatus as claimed in claim 4 wherein each inner body is spaced from the walls of the respective section of the carrier body.

6. Apparatus as claimed in claim 5 wherein each said inner body projects axially within its respective section.

7. Apparatus as claimed in claim 4 wherein said inner body has an outer surface facing said walls of the respective section of the carrier body and the active substance is diffused from the inner body into the substrate from said outer surface towards said walls.

8. Apparatus as claimed in claim 1 wherein said active substance comprises a substance for modifying growth of said agent.

9. Apparatus as claimed in claim 1 wherein said means for introducing active substance into the isolated substrate portions comprises a perforated inner part.

10. Apparatus as claimed in claim 9 wherein said inner part is spaced from the wall of the respective separated section and discharge of the active substance is effected from the space between the wall and the inner part to said substrate via the perforated inner part.

11. Apparatus as claimed in claim 1 comprising means for photometrically analyzing each of said separate regions to determine the extent of the reactivity between the agent and the active substance therein.

12. Apparatus as claimed in claim 1 wherein said active substance is contained in a dispensible article, said apparatus further comprising dispenser means for dispensing the dispensible article into the means which is supported by the carrying body for introducing the active substance into the isolated substrate portions.

13. The invention as claimed in claim 12 wherein said active substance is contained in a dispensible article, the combination further comprising dispenser means for dispensing the dispensible article into the means which is supported by the carrying body for introducing the active substance into the isolated substrate regions.

14. For use in combination with a substrate containing an agent to carry out biological and chemical diffusion tests in microbiological, serological, immunological, clinical-chemical and similar laboratory work: a carrying body including separating partitions defining separate sections in said body, said carrying body having openings which lead into said separate sections, a container for said substrate, said carrying body and container being relatively engageable to cause said substrate to be introduced into said openings and form isolated regions of said substrate in said sections in which said carrying body is immersed to a given depth in the substrate, and means supported by said carrying body for diffusing an active substance into respective isolated regions in the vicinity of immersion of the body in the substrate for producing a substantial equilibrium concentration of the active substance in said confined area, the reactivity of the active substance and agent being the subject of the invention.

15. The invention as claimed in claim 14 wherein said means for diffusing active substance comprises an inner body supported within each section of the carrier body.

16. The invention as claimed in claim 15 wherein each inner body is spaced from the walls of the respective section of the carrier body.

17. The invention as claimed in claim 16 wherein said inner body has an outer surface facing said walls of the respective section of the carrier body and the active substance is diffused from the inner body into the substrate from said outer surface towards said walls.

18. The invention as claimed in claim 14 comprising means for photometrically analyzing each of said isolated regions to determine the extent of the reactivity between the agent and the active substance therein.

19. The invention as claimed in claim 14 wherein the means by which the substrate is introduced into said openings and forms isolated regions of said substrate on said sections comprises an outer container containing said substrate and in which outer container said carrying body is engaged in sealed relation.

20. The invention as claimed in claim 19 wherein said inner body is perforated and discharge of active substance is effected to the substrate via the perforated inner body.

21. The invention as claimed in claim 14 wherein said active substance comprises a substance for modifying growth of said agent.

22. Apparatus for carrying out biological and chemical diffusion tests in microbiological, serological, immunological, and clinical-chemical work, in which at least one active substance is contacted with a substrate containing an agent, the reactivity of the agent and active substance being the subject of investigation, said apparatus comprising a container containing the substrate, an elongated carrying body including at least one first wall and two second walls, the second walls being relatively long compared to said first wall, said carrying body being in sealed contact within the container such that the body forms a region with isolated substrate portion, and means on said first wall for introducing said active substance into the isolated substrate portion by diffusion whereby the diffusion is guided by the relatively long second walls and the length of a reaction zone measured from the first wall is indicative of the reactivity of the agent and active substance.

23. Apparatus as claimed in claim 22 wherein said carrying body has lower edges and is in sealed contact with the container at said lower edges.

24. Apparatus as claimed in claim 22 wherein a plurality of elongated carrying bodies are secured together in juxtaposed relation.

25. A method of carrying out biological and chemical diffusion tests in microbiological, serological, immunological, and clinical-chemical work, in which at least one active substance is contacted with a substrate containing an agent in a container, the reactivity of the agent and active substance being the subject of investigation, said method comprising forming a divided carrying body with respective separated sections, sealably contacting said carrying body with the container such that the sections form separate regions with isolated substrate portions in each of said regions, the carrying body being immersed in the substrate and introducing said active substance into the isolated substrate portions with said carrying body maintained in sealed contact with the container, said introducing of said active substance into the isolated substrate portions being effected by discharging said active substance from within said carrying body into the substrate portions by diffusion in the region of immersion of the carrying body in the substrate whereby the action in said substrate is restricted to said separate regions.

26. A method as claimed in claim 25 wherein the carrying body is in sealed contact with the container at the lower edge of the carrying body.

27. A method as claimed in claim 26 comprising forming an inner body within each section of the carrying body immersed in the respective isolated substrate portions for the introduction of the active substance into the isolated substrate portions.

28. A method as claimed in claim 25 wherein said active substance is dispensed in a disc into said carrying body.

29. A method as claimed in claim 25 comprising effecting at least one secondary application of at least one different active substance to the substrate subsequent to the time after the first substance and agent have been brought into contact with one another.

30. A method as claimed in claim 29 wherein the substance applied to the surface of the substrate is in particulate form.

31. A method as claimed in claim 30 wherein the substance is a bacterium.

32. A method as claimed in claim 29 wherein the substance applied in the secondary application is red blood cells.

33. A method as claimed in claim 29 wherein the substance applied in the secondary application is coated onto inert particles.

34. A method as claimed in claim 25 comprising photometrically analyzing each of said regions to determine the extent of the reactivity between the agent and the active substance.

35. A method as claimed in claim 34 comprising introducing a distinction promoting substance to said substrate to enhance the photometric analyzation of the regions.

36. A method as claimed in claim 34 comprising agitating the substrate after introduction of the active substance thereinto and prior to photometric analysis.

37. A method as claimed in claim 34 comprising incubating the substrate to promote the reactivity of the agent and active substance.

38. A method as claimed in claim 34 wherein the photometric analysis is effected by light scattering.

39. A method for carrying out immunological and similar biochemical examinations in which at least one active substance is contacted with an agent in a container containing a solid or semi-solid substrate, the active substance being selected from the group consisting of the class of antigens and the class of antibodies, said agent being a test dose of a substitutent from the other of said classes, said method comprising forming a divided carrying body with respective separated sections, immersing said carrying body into the substrate in the container such that said sections form separate regions with isolated substrate portions in each of said regions, introducing said active substance into the isolated substrate portions with said carrying body maintained in the container, said introducing of said active substance into the isolated substrate portions being effected by discharging said active substance from within said carrying body into the substrate portions by diffusion in the region of immersion of the carrying body in the substrate and adding the agent to the substrate at the surface thereof after the carrying body is introduced into the container such that the antigens and antibodies undergo agglutination during reaction and form aggregates at the surface of the substrate whereby immunological examination of said classes can be effected at the surface of the substrate.

40. Apparatus for carrying out biological and chemical diffusion tests in microbiological, serological, immunological and clinical chemical work comprising
support means,
a microporous substrate on said support means and including a quantity of agent in relation to the amount of substrate,
said support means confining said substrate to form a confined reaction zone therein, and
distributing means for distributing active substance in liquid form into said substrate,
said distributing means including a layer of porous material also confined by said support means for uniformly distributing the active substance into the substrate to provide a determined uniform quantity of active substance in the confined amount of substrate,
said support means having an opening through which the active substance can be added to said porous material and thereby to the confined substrate,
said quantity of agent and distributing means cooperatively forming a system in which an amount of active substance can be related with a given volumetric amount of substrate to provide rapid diffusion equilibrium in said confined substrate,
said layer of porous material of said distributing means having a surface contact area with said substrate which is coextensive therewith and through which the quantity of active substance is uniformly distributed into said substrate.

41. For use in combination with a substrate containing an agent to carry out biological and chemical diffusion tests in microbiological, serological, immunological, clinical-chemical and similar laboratory work: a tubular carrying body introducible into the substrate, and means associated with said body for diffusing an active substance from said body into the substrate when the tubular body is introduced therein, the reactivity of the active substance and agent being the subject of the investigation, said tubular body comprising magnetically responsive material for the application of magnetic force thereto to move the body in the substrate.

42. The invention as claimed in claim 41 wherein said tubular body comprises a wall, said magnetically responsive material being in said wall.

43. The invention as claimed in claim 41 wherein said tubular body is vacuum packed prior to its introduction into the substrate.

44. The invention as claimed in claim 41 wherein said tubular body has opposite open ends.

45. The invention as claimed in claim 41 wherein said active substance is supported within said tubular body.

46. For use in carrying out biological and chemical diffusion tests in microbiological, serological, immunological, clinical-chemical and similar laboratory work: a carrying body including a wall which is shaped to confine a substantially closed area on one side thereof, means comprising an active substance held on said wall in a position facing into said closed area for diffusing said active substance from said body into the closed area, and a substrate containing an agent confined within said closed area and in which said means is immersed such that said active substance is diffused into the substrate along the depth of immersion therein for producing a substantial equilibrium concentration of the active substance in said confined area, the diffusion of active substance into the substrate taking place from said wall radially inwards along a diffusion front parallel to said wall towards an axis of the body, the diffusion being effected over the depth of penetration of the body into the substrate as measured along said axis, the reactivity of the active substance and agent being the subject of the investigation.

47. The apparatus as claimed in claim 46 wherein said carrying body includes separating partitions therein to form a plurality of separated closed areas, the linings active substances in the respective closed areas having successively varying concentrations.

48. Apparatus for carrying out biological and chemical diffusion tests in microbiological, serological, immunological, clinical-chemical and similar laboratory work comprising a carrying body including a wall which is shaped to confine a substantially closed area on one side thereof, means comprising a lining of an active substance on said wall facing into said closed area for diffusing an active substance from said body into said area to carry out in said closed area a biological or chemical diffusion reaction, and means for introducing into said closed area an agent related to the reaction effected therein, said agent extending to a given depth on said carrying body, said lining extending a height along said wall to diffuse said active substance into said agent along the entire depth of the agent in said carrying body, the diffusion of active substance into the substrate taking place from said lining along a diffusion front parallel to said wall along the depth of the agent in the carrying body.

49. The invention as claimed in claim 47 wherein said means extends a sufficient height along said wall to diffuse said active substance into said agent along the entire depth of the agent in said carrying body.

50. The invention as claimed in claim 49 wherein said lining is a coating on said wall.

51. For carrying out biological and chemical diffusion tests in microbiological, serological, immunological, clinical-chemical and similar laboratory work: a hollow carrying body shaped to confine a substantially closed area on one side thereof, a substrate containing an agent in said carrying body, and means penetrating into said substrate for diffusing an active substance into the substrate for producing a substantial equilibrium concentration of the active substance in said confined area, said closed area having an exposed surface, said means penetrating into said substrate to form a space in said substrate between said means and said hollow carrying body which space surrounds said means, the reactivity of the substance and agent being the subject of the investigation.

52. The invention as claimed in claim 51 wherein said means extends axially within said carrying body.

53. The invention as claimed in claim 52 wherein said means comprises a central body with means for releasing active substance at the outer surface thereof.

54. The invention as claimed in claim 51 wherein said substrate is a liquid.

55. The invention as claimed in claim 54 wherein said means is immersed in said liquid.

56. The invention as claimed in claim 51 wherein said means comprises a solid body.

57. The invention as claimed in claim 56 wherein said active substance is a coating on said solid body.

58. The invention as claimed in claim 51 wherein said means comprises a hollow, perforated body.

59. The invention as claimed in claim 51 wherein said hollow body comprises a wall and said means comprises a hollow perforated inner element spaced from said wall and defining said space therebetween, the active substance being introducible into said space for diffusion into the substrate via the perforated inner element.

60. For use in carrying out biological and chemical diffusion tests: a carrying body having an outer surface, means containing an active substance covering at least a portion of said outer surface of said carrying body, means including a medium containing an agent, the reactivity of the active substance and agent being the subject of investigation, said carrying body being introducible into said medium to define a confined region of said medium with which the active substance is in contact for producing substantially rapid equilibrium concentration of the active substance in said confined region and a container for said medium, said carrying body being introduced into said container to penetrate into the medium and form said confined region of said medium between the carrying body and said container.

61. The combination as claimed in claim 60 comprising magnetically responsive means incorporated in said carrying body and means for applying magnetic force to said magnetically responsive means to draw said carrying body through said substrate.

62. The combination comprising: an article for carrying out testing, said article comprising a test dose of an active substance which may react with an agent of a medium when the article is brought into contact with the medium, and magnetically responsive means incorporated with said test dose as a unitary body; and means for applying a magnetic force to said magnetically responsive means.

63. A method for testing reactions comprising forming a substrate of prescribed composition and including an agent, forming an article containing an active constituent whose reactivity with the agent of the substrate is to be determined by the production of a detectable resule, incorporating magnetically responsive material in said article, bringing the article and substrate into contact with one another and applying an external magnetic force to said article.

64. A method as claimed in claim 63 wherein said magnetic force acts to draw the article through the substrate.

65. Apparatus for carrying out biological and chemical diffusion tests in microbiological, serological, immunological, clinical-chemical and similar laboratory work: comprising a substrate containing an agent, and means forming an isolated reaction region for said substrate and including a coated carrying body introducible into said agent in said isolated region for diffusing active substance from the coating on the carrying body into the substrate, said carrying body being introducible into said substrate as a free body to a given depth, the active substance being diffused into the substrate over the depth of introduction of the carrying body into the substrate for producing a substantial equilibrium concentration of the active substance in said agent, the reactivity of the active substance and agent being the subject of the investigation.

* * * * *

UNITED STATES PATENT AND TRADEMARK OFFICE
CERTIFICATE OF CORRECTION

PATENT NO. : 4,324,859                                    Page 1 of 2
DATED      : April 13, 1982
INVENTOR(S): Rolf Saxholm It is certified that error appears in the above—identified patent and that said Letters Patent is hereby corrected as shown below:

```
Col. 4, lines 38:   change "anaerotic" to--anaerobic--
Col. 5, line 25:    change "as" to--at--
Col. 6, line 57:    change "2,843,450" to--3,843,450--
Col. 9, line 43:    change "element" to--elements--
Col. 14, lines 36-38: rewrite as follows--Fig. 36 is a
                    longitudinal section view through
                    a portion of an assembly including
                    the divided element of Fig. 35.--
Col. 16, line 56:   change "19" to--19a--
Col. 16, line 61:   change "19" to--19a--
Col. 18, line 3:    change "sustrate" to--substrate--
Col. 21, line 54:   after "for" insert--vent holes 906 and--
Col. 23, line 48:   change "positions" to--position--
Col. 23, line 67:   change "900" to--902--

Cancel claim 19.
Claim 13. line 1:   change "12" to--14--
Claim 20. line 1:   change "19" to--15--
Claim 30. line 1:   change "the" to--said different--
          line 2:   after "substance" insert--is--
                    after "substrate" insert--and--
Claim 32. line 1:   change "29" to--30--
Claim 33. line 1:   change "29" to--30--
Claim 37. line 1:   change "34" to--36--
Claim 38. line 1:   change "34" to--36--
Claim 47. line 3:   delete "linings"
Claim 49. line 1:   change "47" to--46--
Claim 50. line 1:   change "49" to--48--
```

UNITED STATES PATENT AND TRADEMARK OFFICE
CERTIFICATE OF CORRECTION

PATENT NO. : 4,324,859

DATED : April 13, 1982

INVENTOR(S) : Rolf Saxholm

Page 2 of 2

It is certified that error appears in the above—identified patent and that said Letters Patent is hereby corrected as shown below:

In the drawings:

Sheet 3 - Fig. 13 : reference numeral "19" should be --19a--
Sheet 5 - Fig. 18: change "42" (down to the left) to --142--
Sheet 12 - Fig. 39: reference numeral 23 should be applied to the four separate sections of element 13a as in Fig. 16.

Signed and Sealed this

Eighteenth Day of February 1986

[SEAL]

Attest:

DONALD J. QUIGG

Attesting Officer

Commissioner of Patents and Trademarks